(12) United States Patent
Haddad

(10) Patent No.: US 8,265,949 B2
(45) Date of Patent: Sep. 11, 2012

(54) CUSTOMIZED PATIENT SURGICAL PLAN

(75) Inventor: Said Haddad, Fort Wayne, IN (US)

(73) Assignee: DePuy Products, Inc., Warsaw, IN (US)

( * ) Notice: Subject to any disclaimer, the term of this patent is extended or adjusted under 35 U.S.C. 154(b) by 786 days.

(21) Appl. No.: 11/862,746

(22) Filed: Sep. 27, 2007

(65) Prior Publication Data
US 2009/0089081 A1    Apr. 2, 2009

(51) Int. Cl.
*G06Q 10/00* (2006.01)
*G06Q 50/00* (2006.01)
(52) U.S. Cl. .................................. 705/2; 705/3
(58) Field of Classification Search .......... 705/2–3; 600/300; 700/97
See application file for complete search history.

(56) References Cited

U.S. PATENT DOCUMENTS

| | | |
|---|---|---|
| 2,702,550 A | 2/1955 | Rowe |
| 3,229,372 A | 1/1966 | Quashnock et al. |
| 3,298,410 A | 1/1967 | Noboru |
| 3,624,747 A | 11/1971 | McKnight et al. |
| 3,685,720 A | 8/1972 | Brady |
| 3,698,017 A | 10/1972 | Scales et al. |
| 3,774,244 A | 11/1973 | Walker |
| 3,840,904 A | 10/1974 | Tronzo |
| 3,869,731 A | 3/1975 | Waugh et al. |
| 3,901,298 A | 8/1975 | Eby |
| 3,903,549 A | 9/1975 | Deyerle |
| 3,920,022 A | 11/1975 | Pastor |
| 3,941,127 A | 3/1976 | Froning |
| 3,965,950 A | 6/1976 | MacDonald |
| 3,994,287 A | 11/1976 | Turp et al. |
| 4,055,862 A | 11/1977 | Farling |
| 4,081,866 A | 4/1978 | Upshaw et al. |
| 4,085,466 A | 4/1978 | Goodfellow et al. |
| 4,140,161 A | 2/1979 | Russo et al. |
| 4,197,886 A | 4/1980 | MacDonald |
| 4,311,145 A | 1/1982 | Esty et al. |
| 4,349,018 A | 9/1982 | Chambers |
| 4,373,709 A | 2/1983 | Whitt |
| 4,386,609 A | 6/1983 | Mongeon |
| 4,400,833 A | 8/1983 | Kurland |
| 4,436,684 A | 3/1984 | White |

(Continued)

FOREIGN PATENT DOCUMENTS

CA    2447694    12/2002

(Continued)

OTHER PUBLICATIONS

"The Vision and Reality of Wearable Computing", XP-002399700, Apr. 1, 2004, 4 pgs.

(Continued)

*Primary Examiner* — Luke Gilligan
(74) *Attorney, Agent, or Firm* — Barnes & Thornburg LLP

(57) ABSTRACT

Systems, methods, and devices are disclosed which generate surgical plans that have been customized for a particular patient. One such system includes a client, a surgical plan system and a computer assisted orthopaedic surgery system. The client generates a surgical plan request that includes data relevant to a patient and an orthopaedic surgical procedure to be performed upon the patient. The surgical plan system receives the surgical plan request and generates a surgical plan that has been customized based upon the data of the surgical plan request. The computer assisted orthopaedic surgery system assists a surgeon performing the orthopaedic surgical procedure per the surgical plan generated by the surgical plan system.

13 Claims, 8 Drawing Sheets

U.S. PATENT DOCUMENTS

| | | |
|---|---|---|
| D273,895 S | 5/1984 | Kenna |
| D274,091 S | 5/1984 | Kenna |
| 4,475,549 A | 10/1984 | Oh |
| 4,501,269 A | 2/1985 | Bagby |
| 4,506,393 A | 3/1985 | Murphy |
| 4,509,518 A | 4/1985 | McGarry et al. |
| 4,534,365 A | 8/1985 | Bonetta et al. |
| 4,545,375 A | 10/1985 | Cline |
| 4,549,555 A | 10/1985 | Fraser et al. |
| 4,562,598 A | 1/1986 | Kranz |
| 4,565,192 A | 1/1986 | Shapiro |
| 4,567,886 A | 2/1986 | Peterson |
| 4,574,794 A | 3/1986 | Cooke et al. |
| 4,583,554 A | 4/1986 | Mittelman et al. |
| 4,583,555 A | 4/1986 | Malcom et al. |
| 4,621,630 A | 11/1986 | Kenna |
| 4,632,111 A | 12/1986 | Roche |
| 4,641,648 A | 2/1987 | Shapiro |
| 4,646,729 A | 3/1987 | Kenna et al. |
| 4,662,372 A | 5/1987 | Sharkany et al. |
| 4,663,720 A | 5/1987 | Duret et al. |
| 4,695,283 A | 9/1987 | Aldinger |
| 4,703,751 A | 11/1987 | Pohl |
| 4,704,686 A | 11/1987 | Aldinger |
| 4,711,233 A | 12/1987 | Brown |
| 4,715,860 A | 12/1987 | Amstutz et al. |
| 4,718,413 A | 1/1988 | Johnson |
| 4,718,916 A | 1/1988 | Morscher |
| 4,719,907 A | 1/1988 | Banko et al. |
| 4,721,104 A | 1/1988 | Kaufman et al. |
| 4,739,751 A | 4/1988 | Sapega et al. |
| 4,787,383 A | 11/1988 | Kenna |
| 4,791,934 A | 12/1988 | Brunnett |
| 4,800,874 A | 1/1989 | David et al. |
| 4,822,365 A | 4/1989 | Walker et al. |
| 4,834,080 A | 5/1989 | Brown |
| 4,834,757 A | 5/1989 | Brantigan |
| 4,838,891 A | 6/1989 | Branemark et al. |
| 4,841,975 A | 6/1989 | Woolson |
| 4,846,161 A | 7/1989 | Roger |
| 4,860,735 A | 8/1989 | Davey et al. |
| 4,888,022 A | 12/1989 | Huebsch |
| 4,893,619 A | 1/1990 | Dale et al. |
| 4,896,663 A | 1/1990 | Vandewalls |
| 4,911,721 A | 3/1990 | Andergaten et al. |
| 4,913,163 A | 4/1990 | Roger et al. |
| 4,927,422 A | 5/1990 | Engelhardt |
| 4,935,023 A | 6/1990 | Whiteside et al. |
| 4,936,852 A | 6/1990 | Kent et al. |
| 4,936,862 A | 6/1990 | Walker et al. |
| 4,952,213 A | 8/1990 | Bowman et al. |
| 4,959,066 A | 9/1990 | Dunn et al. |
| 4,961,740 A | 10/1990 | Ray et al. |
| 4,961,954 A | 10/1990 | Goldberg et al. |
| 4,964,865 A | 10/1990 | Burkhead et al. |
| 4,976,737 A | 12/1990 | Leake |
| 4,979,949 A | 12/1990 | Matsen, III et al. |
| 4,979,957 A | 12/1990 | Hodorek |
| 4,985,037 A | 1/1991 | Petersen |
| 5,002,579 A | 3/1991 | Copf et al. |
| 5,007,912 A | 4/1991 | Albrektsson et al. |
| 5,007,936 A | 4/1991 | Woolson |
| 5,015,247 A | 5/1991 | Michelson |
| 5,030,221 A | 7/1991 | Buechel et al. |
| 5,032,132 A | 7/1991 | Matsen, III et al. |
| 5,035,700 A | 7/1991 | Kenna |
| 5,041,117 A | 8/1991 | Engelhardt |
| 5,053,037 A | 10/1991 | Lackey |
| 5,053,039 A | 10/1991 | Hofmann et al. |
| 5,060,678 A | 10/1991 | Bauman et al. |
| 5,061,286 A | 10/1991 | Lyle |
| 5,062,843 A | 11/1991 | Mahony, III |
| 5,084,050 A | 1/1992 | Draenert |
| 5,086,401 A | 2/1992 | Glassman et al. |
| 5,092,869 A | 3/1992 | Waldron |
| 5,098,383 A | 3/1992 | Hemmy et al. |
| 5,098,436 A | 3/1992 | Ferrante et al. |
| 5,098,437 A | 3/1992 | Kashuba et al. |
| 5,100,689 A | 3/1992 | Goldberg et al. |
| 5,108,401 A | 4/1992 | Insall et al. |
| 5,111,987 A | 5/1992 | Moeinzadeh et al. |
| 5,122,144 A | 6/1992 | Bert et al. |
| 5,123,906 A | 6/1992 | Kelman |
| 5,129,908 A | 7/1992 | Petersen |
| 5,129,909 A | 7/1992 | Sutherland |
| 5,133,660 A | 7/1992 | Fenick |
| 5,133,760 A | 7/1992 | Petersen et al. |
| 5,147,365 A | 9/1992 | Whitlock et al. |
| 5,150,304 A | 9/1992 | Berchem et al. |
| 5,152,744 A | 10/1992 | Krause et al. |
| 5,152,778 A | 10/1992 | Bales, Jr. et al. |
| 5,154,717 A | 10/1992 | Matsen, III et al. |
| 5,171,243 A | 12/1992 | Kashuba et al. |
| 5,171,244 A | 12/1992 | Caspari et al. |
| 5,171,276 A | 12/1992 | Caspari et al. |
| 5,174,300 A | 12/1992 | Bales et al. |
| 5,176,684 A | 1/1993 | Ferrante et al. |
| 5,176,702 A | 1/1993 | Bales et al. |
| 5,186,174 A | 2/1993 | Schloendorff et al. |
| 5,192,327 A | 3/1993 | Brantigan |
| 5,197,488 A | 3/1993 | Kovacevic |
| 5,197,971 A | 3/1993 | Bonutti |
| 5,197,987 A | 3/1993 | Koch et al. |
| 5,207,680 A | 5/1993 | Dietz et al. |
| 5,207,692 A | 5/1993 | Kraus et al. |
| 5,211,165 A | 5/1993 | Dumoulin et al. |
| 5,217,463 A | 6/1993 | Michael |
| 5,228,459 A | 7/1993 | Caspari et al. |
| 5,234,433 A | 8/1993 | Bert et al. |
| 5,242,448 A | 9/1993 | Pettine et al. |
| 5,251,635 A | 10/1993 | Dumoulin et al. |
| 5,255,680 A | 10/1993 | Darrow et al. |
| 5,258,032 A | 11/1993 | Bertin |
| 5,261,915 A | 11/1993 | Durlacher et al. |
| 5,263,498 A | 11/1993 | Caspari et al. |
| 5,263,987 A | 11/1993 | Shah |
| 5,265,610 A | 11/1993 | Darrow |
| 5,269,785 A | 12/1993 | Bonutti |
| 5,273,524 A | 12/1993 | Fox et al. |
| 5,274,565 A | 12/1993 | Reuben |
| 5,275,603 A | 1/1994 | Ferrante et al. |
| 5,282,803 A | 2/1994 | Lackey |
| 5,285,773 A | 2/1994 | Bonutti et al. |
| 5,299,288 A | 3/1994 | Glassman et al. |
| 5,300,077 A | 4/1994 | Howell |
| 5,304,181 A | 4/1994 | Caspari et al. |
| 5,305,244 A | 4/1994 | Newman et al. |
| 5,308,349 A | 5/1994 | Mikhail |
| 5,314,482 A | 5/1994 | Goodfellow et al. |
| 5,320,529 A | 6/1994 | Pompa |
| 5,320,625 A | 6/1994 | Bertin |
| 5,322,505 A | 6/1994 | Krause et al. |
| 5,342,366 A | 8/1994 | Whiteside et al. |
| 5,342,367 A | 8/1994 | Ferrante et al. |
| 5,342,368 A | 8/1994 | Petersen |
| 5,344,423 A | 9/1994 | Dietz et al. |
| 5,344,458 A | 9/1994 | Bonutti |
| 5,360,016 A | 11/1994 | Kovacevic |
| 5,360,446 A | 11/1994 | Kennedy |
| 5,364,402 A | 11/1994 | Mumme et al. |
| 5,368,858 A | 11/1994 | Hunziker |
| 5,370,692 A | 12/1994 | Fink et al. |
| 5,370,699 A | 12/1994 | Hood et al. |
| 5,382,249 A | 1/1995 | Fletcher |
| 5,383,454 A | 1/1995 | Bucholz |
| 5,383,937 A | 1/1995 | Mikhail |
| 5,390,683 A | 2/1995 | Pisharodi |
| 5,395,376 A | 3/1995 | Caspari et al. |
| 5,405,395 A | 4/1995 | Coates |
| 5,408,409 A | 4/1995 | Glassman et al. |
| D358,647 S | 5/1995 | Cohen et al. |
| 5,415,662 A | 5/1995 | Ferrante et al. |
| 5,417,694 A | 5/1995 | Marik et al. |
| 5,423,827 A | 6/1995 | Mumme et al. |
| 5,440,496 A | 8/1995 | Andersson et al. |
| 5,443,475 A | 8/1995 | Auerbach et al. |
| 5,445,639 A | 8/1995 | Kuslich et al. |

| Patent | Date | Inventor |
|---|---|---|
| 5,445,642 A | 8/1995 | McNulty et al. |
| 5,448,489 A | 9/1995 | Reuben |
| 5,452,407 A | 9/1995 | Crook |
| 5,454,816 A | 10/1995 | Ashby |
| 5,456,268 A | 10/1995 | Bonutti |
| 5,458,645 A | 10/1995 | Bertin |
| 5,462,549 A | 10/1995 | Glock |
| 5,470,354 A | 11/1995 | Hershberger et al. |
| 5,472,415 A | 12/1995 | King et al. |
| 5,474,559 A | 12/1995 | Bertin et al. |
| 5,486,178 A | 1/1996 | Hodge |
| 5,490,854 A | 2/1996 | Fisher et al. |
| 5,496,324 A | 3/1996 | Barnes |
| 5,497,933 A | 3/1996 | DeFonzo et al. |
| 5,507,833 A | 4/1996 | Bohn |
| 5,510,066 A | 4/1996 | Fink et al. |
| 5,514,139 A | 5/1996 | Goldstein et al. |
| 5,514,143 A | 5/1996 | Bonutti et al. |
| 5,514,519 A | 5/1996 | Neckers |
| 5,518,680 A | 5/1996 | Cima et al. |
| 5,520,692 A | 5/1996 | Ferrante |
| 5,520,694 A | 5/1996 | Dance et al. |
| 5,520,695 A | 5/1996 | Luckman |
| 5,522,897 A | 6/1996 | King et al. |
| 5,527,317 A | 6/1996 | Ashby et al. |
| 5,539,649 A | 7/1996 | Walsh et al. |
| 5,540,695 A | 7/1996 | Levy |
| 5,549,683 A | 8/1996 | Bonutti |
| 5,554,190 A | 9/1996 | Draenert |
| 5,560,096 A | 10/1996 | Stephens |
| 5,562,674 A | 10/1996 | Stalcup et al. |
| 5,562,675 A | 10/1996 | McNulty et al. |
| 5,569,163 A | 10/1996 | Francis et al. |
| 5,569,261 A | 10/1996 | Marik et al. |
| 5,571,110 A | 11/1996 | Matsen, III et al. |
| 5,578,037 A | 11/1996 | Sanders et al. |
| 5,578,039 A | 11/1996 | Vendrely et al. |
| 5,586,558 A | 12/1996 | Riley |
| 5,593,448 A | 1/1997 | Dong |
| 5,595,703 A | 1/1997 | Swaelens et al. |
| 5,597,379 A | 1/1997 | Haines et al. |
| 5,601,563 A | 2/1997 | Burke et al. |
| 5,607,431 A | 3/1997 | Dudasik et al. |
| 5,609,603 A | 3/1997 | Linden |
| 5,620,448 A | 4/1997 | Puddu |
| 5,624,444 A | 4/1997 | Wixon et al. |
| 5,634,927 A | 6/1997 | Houston |
| 5,643,272 A | 7/1997 | Haines et al. |
| 5,649,947 A | 7/1997 | Auerbach et al. |
| 5,653,714 A | 8/1997 | Dietz et al. |
| 5,658,294 A | 8/1997 | Sederholm |
| 5,662,656 A | 9/1997 | White |
| 5,667,511 A | 9/1997 | Vendrely et al. |
| 5,667,512 A | 9/1997 | Johnson |
| 5,677,107 A | 10/1997 | Neckers |
| 5,681,316 A | 10/1997 | DeOrio et al. |
| 5,681,354 A | 10/1997 | Eckhoff |
| 5,682,886 A | 11/1997 | Delp et al. |
| 5,683,397 A | 11/1997 | Vendrely et al. |
| 5,683,398 A | 11/1997 | Carls et al. |
| 5,688,279 A | 11/1997 | McNulty et al. |
| 5,688,280 A | 11/1997 | Booth, Jr. et al. |
| 5,690,635 A | 11/1997 | Matsen, III et al. |
| 5,701,370 A | 12/1997 | Muhs |
| 5,702,447 A | 12/1997 | Walch et al. |
| 5,702,460 A | 12/1997 | Carls et al. |
| 5,702,475 A | 12/1997 | Zahedi |
| 5,704,941 A | 1/1998 | Jacober et al. |
| 5,707,350 A | 1/1998 | Krause et al. |
| 5,711,299 A | 1/1998 | Manwaring |
| 5,716,360 A | 2/1998 | Baldwin et al. |
| 5,719,743 A | 2/1998 | Jenkins et al. |
| 5,719,744 A | 2/1998 | Jenkins et al. |
| 5,720,752 A | 2/1998 | Elliott et al. |
| 5,722,978 A | 3/1998 | Jenkins, Jr. |
| 5,725,376 A | 3/1998 | Poirier |
| 5,725,593 A | 3/1998 | Caracciolo |
| 5,733,292 A | 3/1998 | Gustilo et al. |
| 5,735,277 A | 4/1998 | Schuster |
| 5,748,767 A | 5/1998 | Raab |
| 5,749,875 A | 5/1998 | Puddu |
| 5,749,876 A | 5/1998 | Duvillier et al. |
| 5,755,803 A | 5/1998 | Haines et al. |
| 5,757,339 A | 5/1998 | Williams et al. |
| 5,762,125 A | 6/1998 | Mastrorio |
| 5,768,134 A | 6/1998 | Swaelens et al. |
| 5,769,855 A | 6/1998 | Bertin et al. |
| 5,776,201 A | 7/1998 | Colleran et al. |
| 5,788,700 A | 8/1998 | Morawa et al. |
| 5,791,212 A | 8/1998 | Han |
| 5,792,143 A | 8/1998 | Samuelson et al. |
| 5,798,924 A | 8/1998 | Eufinger et al. |
| 5,799,055 A | 8/1998 | Peshkin et al. |
| 5,799,099 A | 8/1998 | Wang et al. |
| 5,810,827 A | 9/1998 | Haines et al. |
| 5,810,831 A | 9/1998 | D'Antonio |
| 5,817,097 A | 10/1998 | Howard et al. |
| 5,824,085 A | 10/1998 | Sahay et al. |
| 5,844,656 A | 12/1998 | Ronzani et al. |
| 5,844,824 A | 12/1998 | Newman et al. |
| 5,860,980 A | 1/1999 | Axelson, Jr. et al. |
| 5,860,981 A | 1/1999 | Bertin et al. |
| 5,869,170 A | 2/1999 | Cima et al. |
| 5,871,018 A | 2/1999 | Delp et al. |
| 5,871,493 A | 2/1999 | Sjostrom et al. |
| 5,876,456 A | 3/1999 | Sederholm et al. |
| 5,879,354 A | 3/1999 | Haines et al. |
| 5,879,393 A | 3/1999 | Whiteside et al. |
| 5,879,402 A | 3/1999 | Lawes et al. |
| 5,885,296 A | 3/1999 | Masini |
| 5,885,297 A | 3/1999 | Matsen, III |
| 5,885,298 A | 3/1999 | Herrington et al. |
| 5,895,389 A | 4/1999 | Schenk et al. |
| 5,897,559 A | 4/1999 | Masini |
| 5,899,907 A | 5/1999 | Johnson |
| 5,899,914 A | 5/1999 | Zirps et al. |
| 5,901,060 A | 5/1999 | Schall et al. |
| 5,908,424 A | 6/1999 | Bertin et al. |
| 5,911,723 A | 6/1999 | Ashby et al. |
| 5,911,724 A | 6/1999 | Wehrli |
| 5,913,874 A | 6/1999 | Berns et al. |
| 5,916,219 A | 6/1999 | Matsuno et al. |
| 5,925,049 A | 7/1999 | Gustilo et al. |
| 5,942,370 A | 8/1999 | Neckers |
| 5,967,777 A | 10/1999 | Klein et al. |
| 5,967,980 A | 10/1999 | Ferre et al. |
| 5,976,149 A | 11/1999 | Masini |
| 5,980,526 A | 11/1999 | Johnson et al. |
| 5,989,261 A | 11/1999 | Walker et al. |
| 6,007,537 A | 12/1999 | Burkinshaw et al. |
| 6,012,456 A | 1/2000 | Schuerch |
| 6,019,767 A | 2/2000 | Howell |
| 6,022,350 A | 2/2000 | Ganem |
| 6,024,746 A | 2/2000 | Katz |
| 6,033,415 A | 3/2000 | Mittelstadt et al. |
| 6,034,296 A | 3/2000 | Elvin et al. |
| 6,056,754 A | 5/2000 | Haines et al. |
| 6,056,756 A | 5/2000 | Eng et al. |
| 6,059,831 A | 5/2000 | Braslow et al. |
| 6,063,095 A | 5/2000 | Wang et al. |
| 6,066,075 A | 5/2000 | Poulton |
| 6,077,270 A | 6/2000 | Katz |
| 6,077,287 A | 6/2000 | Taylor et al. |
| 6,080,196 A | 6/2000 | Bertin |
| 6,086,593 A | 7/2000 | Bonutti |
| 6,090,122 A | 7/2000 | Sjostrom et al. |
| 6,096,043 A | 8/2000 | Techiera et al. |
| 6,099,313 A | 8/2000 | Dorken et al. |
| 6,102,850 A | 8/2000 | Wang et al. |
| 6,106,529 A | 8/2000 | Techiera |
| 6,118,845 A | 9/2000 | Simon et al. |
| 6,120,509 A | 9/2000 | Wheeler |
| 6,120,510 A | 9/2000 | Albrektsson et al. |
| 6,120,544 A | 9/2000 | Grundei et al. |
| 6,126,690 A | 10/2000 | Ateshian et al. |
| 6,139,574 A | 10/2000 | Vacanti et al. |
| 6,146,390 A | 11/2000 | Heilbrun et al. |
| 6,156,069 A | 12/2000 | Amstutz |

| | | | | | | |
|---|---|---|---|---|---|---|
| 6,156,070 | A | 12/2000 | Incavo et al. | 6,533,737 | B1 | 3/2003 | Brosseau et al. |
| 6,159,246 | A | 12/2000 | Mendes et al. | 6,535,756 | B1 | 3/2003 | Simon et al. |
| 6,161,080 | A | 12/2000 | Aouni-Ateshian et al. | 6,545,279 | B1 | 4/2003 | Yoshida et al. |
| 6,165,181 | A | 12/2000 | Heilbrun et al. | 6,546,279 | B1 | 4/2003 | Bova et al. |
| 6,167,145 | A | 12/2000 | Foley et al. | 6,552,899 | B2 | 4/2003 | Ronzani et al. |
| 6,176,874 | B1 | 1/2001 | Vacanti et al. | 6,554,837 | B1 | 4/2003 | Hauri et al. |
| 6,177,034 | B1 | 1/2001 | Ferrone | 6,554,838 | B2 | 4/2003 | McGovern et al. |
| 6,185,315 | B1 | 2/2001 | Schmucker et al. | 6,556,008 | B2 | 4/2003 | Thesen |
| 6,187,010 | B1 | 2/2001 | Masini | 6,558,391 | B2 | 5/2003 | Axelson et al. |
| 6,195,615 | B1 | 2/2001 | Lysen | 6,567,681 | B1 | 5/2003 | Lindequist |
| 6,197,064 | B1 | 3/2001 | Haines et al. | 6,575,980 | B1 | 6/2003 | Robie et al. |
| 6,198,794 | B1 | 3/2001 | Peshkin et al. | 6,575,982 | B1 | 6/2003 | Bonutti |
| 6,205,411 | B1 | 3/2001 | DiGioia, III et al. | 6,584,174 | B2 | 6/2003 | Schubert et al. |
| 6,206,927 | B1 | 3/2001 | Fell et al. | 6,591,581 | B2 | 7/2003 | Schmieding |
| 6,214,051 | B1 | 4/2001 | Badorf et al. | 6,602,259 | B1 | 8/2003 | Masini |
| 6,220,122 | B1 | 4/2001 | Forsell | 6,625,563 | B2 | 9/2003 | Kirsch et al. |
| 6,228,121 | B1 | 5/2001 | Khalili | 6,629,999 | B1 | 10/2003 | Serafin, Jr. |
| 6,241,671 | B1 | 6/2001 | Ritter et al. | 6,632,225 | B2 | 10/2003 | Sanford et al. |
| 6,241,735 | B1 | 6/2001 | Marmulla et al. | 6,633,773 | B1 | 10/2003 | Reisfeld |
| 6,244,141 | B1 | 6/2001 | Han | 6,635,073 | B2 | 10/2003 | Bonutti |
| 6,246,900 | B1 | 6/2001 | Cosman et al. | 6,640,127 | B1 | 10/2003 | Kosaka et al. |
| 6,254,604 | B1 | 7/2001 | Howell | 6,642,836 | B1 | 11/2003 | Wang et al. |
| 6,258,127 | B1 | 7/2001 | Schmotzer | 6,646,541 | B1 | 11/2003 | Wang et al. |
| 6,264,698 | B1 | 7/2001 | Lawes et al. | 6,662,036 | B2 | 12/2003 | Cosman |
| 6,273,891 | B1 | 8/2001 | Masini | 6,668,941 | B2 | 12/2003 | Phillips et al. |
| 6,277,136 | B1 | 8/2001 | Bonutti | 6,673,077 | B1 | 1/2004 | Katz |
| 6,285,902 | B1 | 9/2001 | Kienzle, III et al. | 6,676,662 | B1 | 1/2004 | Bagga et al. |
| 6,290,703 | B1 | 9/2001 | Ganem | 6,687,531 | B1 | 2/2004 | Ferre et al. |
| 6,290,704 | B1 | 9/2001 | Burkinshaw et al. | 6,695,848 | B2 | 2/2004 | Haines |
| 6,301,593 | B1 | 10/2001 | Toyosato | 6,697,664 | B2 | 2/2004 | Kienzle, III et al. |
| 6,314,310 | B1 | 11/2001 | Ben-Haim et al. | 6,701,174 | B1 | 3/2004 | Krause et al. |
| 6,319,006 | B1 | 11/2001 | Scherer | 6,702,821 | B2 | 3/2004 | Bonutti |
| 6,322,728 | B1 | 11/2001 | Brodkin et al. | 6,709,462 | B2 | 3/2004 | Hanssen |
| 6,325,806 | B1 | 12/2001 | Fox | 6,711,431 | B2 | 3/2004 | Sarin et al. |
| 6,327,491 | B1 | 12/2001 | Franklin et al. | 6,711,432 | B1 | 3/2004 | Krause et al. |
| 6,341,231 | B1 | 1/2002 | Ferre et al. | 6,712,824 | B2 | 3/2004 | Millard et al. |
| 6,343,987 | B2 | 2/2002 | Hayama et al. | 6,712,856 | B1 | 3/2004 | Carignan et al. |
| 6,351,659 | B1 | 2/2002 | Vilsmeier | 6,716,249 | B2 | 4/2004 | Hyde |
| 6,354,011 | B1 | 3/2002 | Albrecht | 6,724,922 | B1 | 4/2004 | Vilsmeier |
| 6,361,506 | B1 | 3/2002 | Saenger et al. | 6,725,077 | B1 | 4/2004 | Balloni et al. |
| 6,370,224 | B1 | 4/2002 | Simon et al. | 6,725,080 | B2 | 4/2004 | Melkent et al. |
| 6,382,975 | B1 | 5/2002 | Poirier | 6,738,656 | B1 | 5/2004 | Ferre et al. |
| 6,383,228 | B1 | 5/2002 | Schmotzer | 6,738,657 | B1 | 5/2004 | Franklin et al. |
| 6,391,251 | B1 | 5/2002 | Keicher et al. | 6,740,092 | B2 | 5/2004 | Lombardo et al. |
| 6,395,005 | B1 | 5/2002 | Lovell | 6,749,638 | B1 | 6/2004 | Saladino |
| 6,405,072 | B1 | 6/2002 | Cosman | 6,750,653 | B1 | 6/2004 | Zou et al. |
| 6,406,495 | B1 | 6/2002 | Schoch | 6,770,078 | B2 | 8/2004 | Bonutti |
| 6,409,722 | B1 | 6/2002 | Hoey et al. | 6,772,026 | B2 | 8/2004 | Bradbury et al. |
| 6,421,232 | B2 | 7/2002 | Sallam | 6,780,190 | B2 | 8/2004 | Maroney |
| 6,424,856 | B1 | 7/2002 | Vilsmeier | 6,786,930 | B2 | 9/2004 | Biscup |
| 6,427,698 | B1 | 8/2002 | Yoon | 6,798,391 | B2 | 9/2004 | Peterson, III |
| 6,430,434 | B1 | 8/2002 | Mittelstadt | 6,799,066 | B2 | 9/2004 | Steines et al. |
| 6,434,415 | B1 | 8/2002 | Foley et al. | 6,814,735 | B1 | 11/2004 | Zimgibl et al. |
| 6,442,416 | B1 | 8/2002 | Schultz | 6,827,723 | B2 | 12/2004 | Carson |
| D462,767 | S | 9/2002 | Meyer et al. | 6,847,336 | B1 | 1/2005 | Lemelson |
| 6,445,943 | B1 | 9/2002 | Ferre et al. | 6,859,660 | B2 | 2/2005 | Vilsmeier |
| 6,454,811 | B1 | 9/2002 | Sherwood et al. | 6,873,867 | B2 | 3/2005 | Vilsmeier |
| 6,458,135 | B1 | 10/2002 | Harwin et al. | 6,892,090 | B2 | 5/2005 | Verard et al. |
| 6,459,948 | B1 | 10/2002 | Ateshian et al. | 6,905,514 | B2 | 6/2005 | Carignan et al. |
| 6,461,359 | B1 | 10/2002 | Tribus et al. | 6,916,324 | B2 | 7/2005 | Sanford et al. |
| 6,463,351 | B1 | 10/2002 | Clynch | 6,920,347 | B2 | 7/2005 | Simon et al. |
| 6,463,361 | B1 | 10/2002 | Wang | 6,923,817 | B2 | 8/2005 | Carson et al. |
| 6,468,280 | B1 | 10/2002 | Saenger et al. | 6,923,831 | B2 | 8/2005 | Fell et al. |
| 6,468,289 | B1 | 10/2002 | Bonutti | 6,932,842 | B1 | 8/2005 | Litschko et al. |
| 6,474,341 | B1 | 11/2002 | Hunter et al. | 6,934,575 | B2 | 8/2005 | Ferre et al. |
| 6,478,799 | B1 | 11/2002 | Williamson | 6,942,475 | B2 | 9/2005 | Ensign et al. |
| 6,482,209 | B1 | 11/2002 | Engh et al. | 6,944,518 | B2 | 9/2005 | Roose |
| 6,490,467 | B1 | 12/2002 | Bucholz et al. | 6,945,976 | B2 | 9/2005 | Ball et al. |
| 6,491,702 | B2 | 12/2002 | Heilbrun et al. | 6,947,786 | B2 | 9/2005 | Simon et al. |
| 6,493,573 | B1 | 12/2002 | Martinelli et al. | 6,953,480 | B2 | 10/2005 | Mears et al. |
| 6,496,099 | B2 | 12/2002 | Wang et al. | 6,968,846 | B2 | 11/2005 | Viswanathan |
| 6,499,488 | B1 | 12/2002 | Hunter et al. | 6,978,166 | B2 | 12/2005 | Foley et al. |
| 6,503,255 | B1 | 1/2003 | Albrektsson et al. | 6,979,299 | B2 | 12/2005 | Peabody et al. |
| 6,510,334 | B1 | 1/2003 | Schuster et al. | 6,990,220 | B2 | 1/2006 | Ellis et al. |
| 6,514,259 | B2 | 2/2003 | Picard et al. | 6,994,549 | B2 | 2/2006 | Brodkin et al. |
| 6,516,212 | B1 | 2/2003 | Bladen et al. | 7,029,477 | B2 | 4/2006 | Grimm |
| 6,520,964 | B2 | 2/2003 | Tallarida et al. | 7,029,479 | B2 | 4/2006 | Tallarida et al. |
| 6,530,958 | B1 | 3/2003 | Cima et al. | 7,048,741 | B2 | 5/2006 | Swanson |
| 6,532,482 | B1 | 3/2003 | Toyosato | 7,050,877 | B2 | 5/2006 | Iseki et al. |

| | | |
|---|---|---|
| 7,060,074 B2 | 6/2006 | Rosa et al. |
| RE39,301 E | 9/2006 | Bertin |
| 7,104,997 B2 | 9/2006 | Lionberger et al. |
| 7,105,026 B2 | 9/2006 | Johnson et al. |
| 7,115,131 B2 | 10/2006 | Engh et al. |
| 7,141,053 B2 | 11/2006 | Rosa et al. |
| 7,172,597 B2 | 2/2007 | Sanford |
| 7,172,599 B2 | 2/2007 | Steffensmeier et al. |
| 7,175,435 B2 | 2/2007 | Andersson et al. |
| 7,176,466 B2 | 2/2007 | Rousso et al. |
| 7,184,814 B2 | 2/2007 | Lang et al. |
| 7,194,295 B2 | 3/2007 | Vilsmeier |
| 7,198,628 B2 | 4/2007 | Ondrla et al. |
| 7,239,908 B1 | 7/2007 | Alexander et al. |
| 7,255,702 B2 | 8/2007 | Serra et al. |
| 7,258,701 B2 | 8/2007 | Aram et al. |
| 7,261,719 B1 | 8/2007 | Twomey et al. |
| 7,261,729 B2 | 8/2007 | Spencer |
| 7,275,218 B2 | 9/2007 | Petrella et al. |
| 7,282,054 B2 | 10/2007 | Steffensmeier et al. |
| 7,294,133 B2 | 11/2007 | Zink et al. |
| 7,297,164 B2 | 11/2007 | Johnson et al. |
| 7,309,339 B2 | 12/2007 | Cusick et al. |
| 7,371,260 B2 | 5/2008 | Malinin |
| 7,383,164 B2 | 6/2008 | Aram et al. |
| 7,388,972 B2 | 6/2008 | Kitson |
| 7,392,076 B2 | 6/2008 | Moctezuma de La Barrera |
| 7,427,272 B2 | 9/2008 | Richard et al. |
| 7,474,223 B2 | 1/2009 | Nycz et al. |
| 7,481,780 B2 | 1/2009 | De Guise et al. |
| 7,488,324 B1 | 2/2009 | Metzger et al. |
| 7,527,631 B2 | 5/2009 | Maroney et al. |
| 7,534,263 B2 | 5/2009 | Burdulis, Jr. et al. |
| 7,539,243 B1 | 5/2009 | Toifl et al. |
| 7,542,791 B2 | 6/2009 | Mire et al. |
| 7,575,602 B2 | 8/2009 | Amirouche et al. |
| 7,582,091 B2 | 9/2009 | Duncan et al. |
| 7,591,821 B2 | 9/2009 | Kelman |
| 7,601,155 B2 | 10/2009 | Peterson |
| 7,604,639 B2 | 10/2009 | Swanson |
| 7,611,516 B2 | 11/2009 | Maroney |
| 7,618,451 B2 | 11/2009 | Berez et al. |
| 7,621,915 B2 | 11/2009 | Frederick et al. |
| 7,625,409 B2 | 12/2009 | Saltzman et al. |
| 7,634,119 B2 | 12/2009 | Tsougarakis et al. |
| 7,651,501 B2 | 1/2010 | Penenberg et al. |
| 7,661,170 B2 | 2/2010 | Goode et al. |
| 7,695,477 B2 | 4/2010 | Creger et al. |
| 7,704,253 B2 | 4/2010 | Bastian et al. |
| 7,717,956 B2 | 5/2010 | Lang |
| 7,780,672 B2 | 8/2010 | Metzger |
| 7,796,791 B2 | 9/2010 | Tsougarakis et al. |
| 7,799,077 B2 | 9/2010 | Lang et al. |
| 7,806,896 B1 | 10/2010 | Bonutti |
| 7,824,181 B2 | 11/2010 | Sers |
| 7,887,595 B1 | 2/2011 | Pimenta |
| 7,935,119 B2 | 5/2011 | Ammann et al. |
| 7,963,968 B2 | 6/2011 | Dees, Jr. |
| 7,967,868 B2 | 6/2011 | White et al. |
| 7,981,158 B2 | 7/2011 | Fitz et al. |
| 2001/0005797 A1 | 6/2001 | Barlow et al. |
| 2001/0018589 A1 | 8/2001 | Muller |
| 2001/0020143 A1 | 9/2001 | Stark |
| 2001/0034554 A1 | 10/2001 | Pappas |
| 2001/0037155 A1 | 11/2001 | Merchant |
| 2001/0039421 A1 | 11/2001 | Heibrun et al. |
| 2002/0007294 A1 | 1/2002 | Bradbury et al. |
| 2002/0024450 A1 | 2/2002 | Townsend et al. |
| 2002/0029038 A1 | 3/2002 | Haines |
| 2002/0029045 A1 | 3/2002 | Bonutti |
| 2002/0052606 A1 | 5/2002 | Bonutti |
| 2002/0059049 A1 | 5/2002 | Bradbury et al. |
| 2002/0082741 A1 | 6/2002 | Mazumder et al. |
| 2002/0087062 A1 | 7/2002 | Schmidt et al. |
| 2002/0087274 A1 | 7/2002 | Alexander et al. |
| 2002/0143279 A1 | 10/2002 | Porier |
| 2002/0147415 A1 | 10/2002 | Martelli |
| 2002/0173797 A1 | 11/2002 | Van Zile et al. |
| 2002/0183610 A1 | 12/2002 | Foley et al. |
| 2002/0183760 A1 | 12/2002 | McGovern et al. |
| 2002/0188194 A1 | 12/2002 | Cosman |
| 2002/0198529 A1 | 12/2002 | Masini |
| 2002/0198531 A1 | 12/2002 | Millard et al. |
| 2003/0009234 A1 | 1/2003 | Treacy et al. |
| 2003/0011624 A1 | 1/2003 | Ellis |
| 2003/0018338 A1 | 1/2003 | Axelson et al. |
| 2003/0028196 A1 | 2/2003 | Bonutti |
| 2003/0055502 A1 | 3/2003 | Lang et al. |
| 2003/0069897 A1 | 4/2003 | Roy et al. |
| 2003/0088179 A1 | 5/2003 | Seeley et al. |
| 2003/0100906 A1 | 5/2003 | Rosa et al. |
| 2003/0100907 A1 | 5/2003 | Rosa et al. |
| 2003/0109784 A1 | 6/2003 | Loh et al. |
| 2003/0120183 A1 | 6/2003 | Simmons |
| 2003/0130665 A1 | 7/2003 | Pinczewski |
| 2003/0158606 A1 | 8/2003 | Coon et al. |
| 2003/0171757 A1 | 9/2003 | Coon et al. |
| 2003/0181935 A1 | 9/2003 | Gardeski et al. |
| 2003/0212403 A1 | 11/2003 | Swanson |
| 2003/0216669 A1 | 11/2003 | Lang et al. |
| 2003/0216741 A1 | 11/2003 | Sanford et al. |
| 2003/0220641 A1 | 11/2003 | Thelen et al. |
| 2003/0225413 A1 | 12/2003 | Sanford et al. |
| 2004/0039259 A1 | 2/2004 | Krause et al. |
| 2004/0039395 A1 | 2/2004 | Coon et al. |
| 2004/0068187 A1 | 4/2004 | Krause et al. |
| 2004/0073279 A1 | 4/2004 | Malackowski et al. |
| 2004/0092932 A1 | 5/2004 | Aubin et al. |
| 2004/0098133 A1 | 5/2004 | Carignan |
| 2004/0102785 A1 | 5/2004 | Hodorek et al. |
| 2004/0102852 A1 | 5/2004 | Johnson |
| 2004/0102866 A1 | 5/2004 | Harris et al. |
| 2004/0106926 A1 | 6/2004 | Leitner et al. |
| 2004/0115586 A1 | 6/2004 | Andreiko |
| 2004/0122439 A1 | 6/2004 | Dwyer et al. |
| 2004/0122787 A1 | 6/2004 | Avinash et al. |
| 2004/0122790 A1 | 6/2004 | Walker et al. |
| 2004/0124964 A1 | 7/2004 | Wang et al. |
| 2004/0128026 A1 | 7/2004 | Harris et al. |
| 2004/0133276 A1 | 7/2004 | Lang et al. |
| 2004/0138670 A1 | 7/2004 | Metzger |
| 2004/0138754 A1 | 7/2004 | Lang et al. |
| 2004/0143336 A1 | 7/2004 | Burkinshaw |
| 2004/0147927 A1 | 7/2004 | Tsougarakis et al. |
| 2004/0153079 A1 | 8/2004 | Tsougarakis et al. |
| 2004/0153087 A1 | 8/2004 | Sanford et al. |
| 2004/0158254 A1 | 8/2004 | Eisermann |
| 2004/0162619 A1 | 8/2004 | Blaylock et al. |
| 2004/0167390 A1 | 8/2004 | Alexander et al. |
| 2004/0171924 A1 | 9/2004 | Mire et al. |
| 2004/0172137 A1 | 9/2004 | Blaylock et al. |
| 2004/0181144 A1 | 9/2004 | Cinquin et al. |
| 2004/0185422 A1 | 9/2004 | Orth et al. |
| 2004/0204760 A1 | 10/2004 | Fitz et al. |
| 2004/0220583 A1 | 11/2004 | Pieczynski |
| 2004/0236424 A1 | 11/2004 | Berez et al. |
| 2004/0243481 A1 | 12/2004 | Bradbury et al. |
| 2004/0249385 A1 | 12/2004 | Faoro |
| 2004/0249675 A1 | 12/2004 | Stark et al. |
| 2004/0254584 A1 | 12/2004 | Sarin et al. |
| 2004/0260301 A1 | 12/2004 | Lionberger |
| 2005/0015003 A1 | 1/2005 | Lachner et al. |
| 2005/0015022 A1 | 1/2005 | Richard et al. |
| 2005/0027303 A1 | 2/2005 | Lionberger |
| 2005/0027361 A1 | 2/2005 | Reiley |
| 2005/0037320 A1 | 2/2005 | Poirier |
| 2005/0043835 A1 | 2/2005 | Christensen |
| 2005/0043837 A1 | 2/2005 | Rubbert et al. |
| 2005/0049524 A1 | 3/2005 | Lefevre et al. |
| 2005/0049603 A1 | 3/2005 | Calton et al. |
| 2005/0059873 A1 | 3/2005 | Glozman et al. |
| 2005/0065628 A1 | 3/2005 | Roose |
| 2005/0070897 A1 | 3/2005 | Petersen |
| 2005/0075641 A1 | 4/2005 | Singhatat et al. |
| 2005/0096535 A1 | 5/2005 | de la Barrera |
| 2005/0113840 A1 | 5/2005 | Metzger et al. |
| 2005/0113841 A1 | 5/2005 | Sheldon et al. |
| 2005/0113846 A1 | 5/2005 | Carson |

| | | |
|---|---|---|
| 2005/0119664 A1 | 6/2005 | Carignan |
| 2005/0131662 A1 | 6/2005 | Ascenzi |
| 2005/0133955 A1 | 6/2005 | Christensen |
| 2005/0137708 A1 | 6/2005 | Clark |
| 2005/0148843 A1 | 7/2005 | Roose |
| 2005/0149042 A1 | 7/2005 | Metzger |
| 2005/0170311 A1 | 8/2005 | Tardieu |
| 2005/0171545 A1 | 8/2005 | Walsh et al. |
| 2005/0177170 A1 | 8/2005 | Fisher et al. |
| 2005/0182315 A1 | 8/2005 | Ritter et al. |
| 2005/0203536 A1 | 9/2005 | Laffargue et al. |
| 2005/0203540 A1 | 9/2005 | Broyles |
| 2025/0203540 | 9/2005 | Broyles |
| 2005/0222573 A1 | 10/2005 | Branch et al. |
| 2005/0234461 A1 | 10/2005 | Burdulis et al. |
| 2005/0234468 A1 | 10/2005 | Carson |
| 2005/0244239 A1 | 11/2005 | Shimp |
| 2005/0245934 A1 | 11/2005 | Tuke et al. |
| 2005/0245936 A1 | 11/2005 | Tuke et al. |
| 2005/0261697 A1 | 11/2005 | Canonaco et al. |
| 2005/0267584 A1 | 12/2005 | Burdulis et al. |
| 2005/0273113 A1 | 12/2005 | Kuczynski |
| 2005/0273114 A1 | 12/2005 | Novak |
| 2005/0283252 A1 | 12/2005 | Coon et al. |
| 2005/0283253 A1 | 12/2005 | Coon et al. |
| 2006/0004284 A1 | 1/2006 | Grunschlager et al. |
| 2006/0015120 A1 | 1/2006 | Richard et al. |
| 2006/0030853 A1 | 2/2006 | Haines |
| 2006/0052725 A1 | 3/2006 | Santilli |
| 2006/0058803 A1 | 3/2006 | Cuckler et al. |
| 2006/0058884 A1 | 3/2006 | Aram et al. |
| 2006/0058886 A1 | 3/2006 | Wozencroft |
| 2006/0089621 A1 | 4/2006 | Fard |
| 2006/0093988 A1 | 5/2006 | Swaelens et al. |
| 2006/0094951 A1 | 5/2006 | Dean et al. |
| 2006/0095049 A1 | 5/2006 | Zannis et al. |
| 2006/0100832 A1 | 5/2006 | Bowman |
| 2006/0111722 A1 | 5/2006 | Bouadi |
| 2006/0122616 A1 | 6/2006 | Bennett |
| 2006/0136058 A1 | 6/2006 | Pietrzak |
| 2006/0142657 A1 | 6/2006 | Quaid et al. |
| 2006/0142671 A1 | 6/2006 | Solak |
| 2006/0142774 A1 | 6/2006 | Metzger |
| 2006/0142778 A1 | 6/2006 | Dees |
| 2006/0155380 A1 | 7/2006 | Clemow |
| 2006/0161167 A1 | 7/2006 | Myers |
| 2006/0184177 A1 | 8/2006 | Echeverri |
| 2006/0190086 A1 | 8/2006 | Clemow et al. |
| 2006/0195198 A1 | 8/2006 | James |
| 2006/0204932 A1 | 9/2006 | Haymann et al. |
| 2006/0210644 A1 | 9/2006 | Levin |
| 2006/0229723 A1 | 10/2006 | Van Hoeck |
| 2006/0235421 A1 | 10/2006 | Rosa et al. |
| 2006/0271058 A1 | 11/2006 | Ashton |
| 2006/0276796 A1 | 12/2006 | Creger et al. |
| 2006/0276797 A1 | 12/2006 | Botimer |
| 2006/0287733 A1 | 12/2006 | Bonutti |
| 2007/0006887 A1 | 1/2007 | Frank |
| 2007/0015995 A1 | 1/2007 | Lang et al. |
| 2007/0016209 A1 | 1/2007 | Ammann et al. |
| 2007/0027680 A1 | 2/2007 | Ashley et al. |
| 2007/0059665 A1 | 3/2007 | Orentlicher et al. |
| 2007/0066917 A1 | 3/2007 | Hodorek et al. |
| 2007/0083209 A1 | 4/2007 | Schenberger |
| 2007/0083214 A1 | 4/2007 | Duncan et al. |
| 2007/0083266 A1 | 4/2007 | Lang |
| 2007/0100258 A1 | 5/2007 | Shoham et al. |
| 2007/0100462 A1 | 5/2007 | Lang et al. |
| 2007/0118055 A1 | 5/2007 | McCombs |
| 2007/0118243 A1 | 5/2007 | Schroeder et al. |
| 2007/0156066 A1 | 7/2007 | McGinley et al. |
| 2007/0162039 A1 | 7/2007 | Wozencroft |
| 2007/0167741 A1* | 7/2007 | Sherman et al. ............... 600/424 |
| 2007/0173946 A1 | 7/2007 | Bonutti |
| 2007/0185498 A2 | 8/2007 | Lavallee |
| 2007/0198022 A1 | 8/2007 | Lang et al. |
| 2007/0203430 A1 | 8/2007 | Lang et al. |
| 2007/0203605 A1 | 8/2007 | Melton et al. |
| 2007/0213738 A1 | 9/2007 | Martin et al. |
| 2007/0219639 A1 | 9/2007 | Otto et al. |
| 2007/0225719 A1 | 9/2007 | Stone et al. |
| 2007/0226986 A1 | 10/2007 | Park et al. |
| 2007/0233121 A1 | 10/2007 | Carson et al. |
| 2007/0233136 A1 | 10/2007 | Wozencroft |
| 2007/0233140 A1 | 10/2007 | Metzger et al. |
| 2007/0233141 A1 | 10/2007 | Park |
| 2007/0233269 A1 | 10/2007 | Steines et al. |
| 2007/0233272 A1 | 10/2007 | Boyce et al. |
| 2007/0238069 A1 | 10/2007 | Lovald et al. |
| 2007/0239282 A1 | 10/2007 | Caylor et al. |
| 2007/0239481 A1 | 10/2007 | DiSilvestro et al. |
| 2007/0250169 A1 | 10/2007 | Lang |
| 2007/0253617 A1 | 11/2007 | Arata |
| 2007/0255288 A1 | 11/2007 | Mahfouz et al. |
| 2007/0255412 A1 | 11/2007 | Hajaj et al. |
| 2007/0276224 A1 | 11/2007 | Lang et al. |
| 2007/0276400 A1 | 11/2007 | Moore et al. |
| 2007/0276501 A1 | 11/2007 | Betz et al. |
| 2007/0282451 A1 | 12/2007 | Metzger et al. |
| 2007/0288030 A1* | 12/2007 | Metzger et al. ............... 606/87 |
| 2008/0009952 A1 | 1/2008 | Hodge |
| 2008/0015602 A1 | 1/2008 | Axelson |
| 2008/0015605 A1 | 1/2008 | Collazo |
| 2008/0015607 A1 | 1/2008 | D'Alessio |
| 2008/0021299 A1 | 1/2008 | Meulink |
| 2008/0021567 A1 | 1/2008 | Meulink et al. |
| 2008/0027563 A1 | 1/2008 | Johnson |
| 2008/0051910 A1 | 2/2008 | Kammerzell et al. |
| 2008/0058945 A1 | 3/2008 | Hajaj et al. |
| 2008/0058947 A1 | 3/2008 | Earl et al. |
| 2008/0114370 A1 | 5/2008 | Schoenefeld |
| 2008/0140081 A1 | 6/2008 | Heavener |
| 2008/0140209 A1 | 6/2008 | Iannotti et al. |
| 2008/0146969 A1 | 6/2008 | Kurtz |
| 2008/0147072 A1 | 6/2008 | Park et al. |
| 2008/0161815 A1 | 7/2008 | Schoenefeld et al. |
| 2008/0172125 A1 | 7/2008 | Ek |
| 2008/0183177 A1 | 7/2008 | Fox et al. |
| 2008/0195099 A1 | 8/2008 | Minas |
| 2008/0195107 A1 | 8/2008 | Cuckler et al. |
| 2008/0195216 A1 | 8/2008 | Philipp |
| 2008/0208200 A1 | 8/2008 | Crofford |
| 2008/0215059 A1 | 9/2008 | Carignan et al. |
| 2008/0228189 A1 | 9/2008 | Fox et al. |
| 2008/0234664 A1 | 9/2008 | May et al. |
| 2008/0234683 A1 | 9/2008 | May |
| 2008/0234685 A1 | 9/2008 | Gjerde |
| 2008/0234833 A1 | 9/2008 | Bandoh et al. |
| 2008/0243127 A1 | 10/2008 | Lang et al. |
| 2008/0257363 A1 | 10/2008 | Schoenefeld et al. |
| 2008/0262624 A1 | 10/2008 | White et al. |
| 2008/0269906 A1 | 10/2008 | Iannotti et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287954 A1 | 11/2008 | Kunz et al. |
| 2008/0294266 A1 | 11/2008 | Steinberg |
| 2008/0300600 A1 | 12/2008 | Guelat et al. |
| 2008/0306558 A1 | 12/2008 | Hakki |
| 2008/0312659 A1 | 12/2008 | Metzger et al. |
| 2008/0319448 A1 | 12/2008 | Lavallee et al. |
| 2009/0012526 A1 | 1/2009 | Fletcher |
| 2009/0018546 A1 | 1/2009 | Daley |
| 2009/0024131 A1 | 1/2009 | Metzger et al. |
| 2009/0043556 A1 | 2/2009 | Axelson et al. |
| 2009/0076371 A1 | 3/2009 | Lang et al. |
| 2009/0076512 A1 | 3/2009 | Ammann et al. |
| 2009/0082770 A1 | 3/2009 | Worner et al. |
| 2009/0087276 A1 | 4/2009 | Rose |
| 2009/0088674 A1 | 4/2009 | Caillouette et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |

| | | | |
|---|---|---|---|
| 2009/0088763 A1 | 4/2009 | Aram et al. | |
| 2009/0089034 A1 | 4/2009 | Penney et al. | |
| 2009/0089081 A1 | 4/2009 | Haddad | |
| 2009/0093816 A1 | 4/2009 | Roose et al. | |
| 2009/0099567 A1 | 4/2009 | Zajac | |
| 2009/0105837 A1 | 4/2009 | Lafosse et al. | |
| 2009/0118736 A1 | 5/2009 | Kreuzer | |
| 2009/0131941 A1 | 5/2009 | Park et al. | |
| 2009/0131942 A1 | 5/2009 | Aker et al. | |
| 2009/0138020 A1 | 5/2009 | Park et al. | |
| 2009/0149965 A1 | 6/2009 | Quaid | |
| 2009/0149977 A1 | 6/2009 | Schendel | |
| 2009/0151736 A1 | 6/2009 | Belcher et al. | |
| 2009/0157083 A1 | 6/2009 | Park et al. | |
| 2009/0163922 A1 | 6/2009 | Meridew et al. | |
| 2009/0163923 A1 | 6/2009 | Flett et al. | |
| 2009/0164024 A1 | 6/2009 | Rudan et al. | |
| 2009/0187193 A1 | 7/2009 | Maroney et al. | |
| 2009/0209884 A1 | 8/2009 | Van Vorhis et al. | |
| 2009/0209961 A1 | 8/2009 | Ferrante et al. | |
| 2009/0222014 A1 | 9/2009 | Bojarski et al. | |
| 2009/0222015 A1 | 9/2009 | Park et al. | |
| 2009/0222016 A1 | 9/2009 | Park et al. | |
| 2009/0228016 A1 | 9/2009 | Alvarez et al. | |
| 2009/0234360 A1 | 9/2009 | Alexander | |
| 2009/0248044 A1 | 10/2009 | Amiot et al. | |
| 2009/0254093 A1 | 10/2009 | White et al. | |
| 2009/0254367 A1 | 10/2009 | Belcher et al. | |
| 2009/0270868 A1 | 10/2009 | Park et al. | |
| 2009/0274350 A1 | 11/2009 | Pavlovskaia et al. | |
| 2009/0306676 A1 | 12/2009 | Lang et al. | |
| 2009/0307893 A1 | 12/2009 | Burdulis, Jr. et al. | |
| 2009/0318836 A1 | 12/2009 | Stone et al. | |
| 2010/0016947 A1 | 1/2010 | Dobak et al. | |
| 2010/0016984 A1 | 1/2010 | Trabish | |
| 2010/0016986 A1 | 1/2010 | Trabish | |
| 2010/0023015 A1 | 1/2010 | Park | |
| 2010/0030231 A1 | 2/2010 | Revie et al. | |
| 2010/0042105 A1 | 2/2010 | Park et al. | |
| 2010/0049195 A1 | 2/2010 | Park et al. | |
| 2010/0076439 A1 | 3/2010 | Hatch | |
| 2010/0076505 A1 | 3/2010 | Borja | |
| 2010/0076563 A1 | 3/2010 | Otto et al. | |
| 2010/0076571 A1 | 3/2010 | Hatch | |
| 2010/0082034 A1 | 4/2010 | Remia | |
| 2010/0082035 A1 | 4/2010 | Keefer | |
| 2010/0087829 A1 | 4/2010 | Metzger et al. | |
| 2010/0094295 A1 | 4/2010 | Schnieders et al. | |
| 2010/0105011 A1 | 4/2010 | Karkar et al. | |
| 2010/0121335 A1 | 5/2010 | Penenberg et al. | |
| 2010/0137869 A1 | 6/2010 | Borja et al. | |
| 2010/0137924 A1 | 6/2010 | Tuke et al. | |
| 2010/0145343 A1 | 6/2010 | Johnson et al. | |
| 2010/0145344 A1 | 6/2010 | Jordan et al. | |
| 2010/0152782 A1 | 6/2010 | Stone et al. | |
| 2010/0160917 A1 | 6/2010 | Fitz et al. | |
| 2010/0168754 A1 | 7/2010 | Fitz et al. | |
| 2010/0168857 A1 | 7/2010 | Hatch | |
| 2010/0185202 A1 | 7/2010 | Lester et al. | |
| 2010/0191244 A1 | 7/2010 | White et al. | |
| 2010/0212138 A1 | 8/2010 | Carroll et al. | |
| 2010/0217109 A1 | 8/2010 | Belcher | |
| 2010/0217270 A1 | 8/2010 | Polinski et al. | |
| 2010/0217338 A1 | 8/2010 | Carroll et al. | |
| 2010/0228257 A1 | 9/2010 | Bonutti | |
| 2010/0249657 A1 | 9/2010 | Nycz et al. | |
| 2010/0249796 A1 | 9/2010 | Nycz | |
| 2010/0262150 A1 | 10/2010 | Lian | |
| 2010/0274253 A1 | 10/2010 | Ure | |
| 2010/0281678 A1 | 11/2010 | Burdulis, Jr. et al. | |
| 2010/0286700 A1 | 11/2010 | Snider et al. | |
| 2010/0292743 A1 | 11/2010 | Singhal et al. | |
| 2010/0305573 A1 | 12/2010 | Fitz et al. | |
| 2010/0305574 A1 | 12/2010 | Fitz et al. | |
| 2010/0324692 A1 | 12/2010 | Uthgenannt et al. | |
| 2011/0004317 A1 | 1/2011 | Hacking et al. | |
| 2011/0015636 A1 | 1/2011 | Katrana et al. | |
| 2011/0015639 A1 | 1/2011 | Metzger et al. | |
| 2011/0029091 A1 | 2/2011 | Bojarski et al. | |
| 2011/0029116 A1 | 2/2011 | Jordan et al. | |
| 2011/0046735 A1 | 2/2011 | Metzger et al. | |
| 2011/0054478 A1 | 3/2011 | Vanasse et al. | |
| 2011/0066193 A1 | 3/2011 | Lang et al. | |
| 2011/0071528 A1 | 3/2011 | Carson | |
| 2011/0071529 A1 | 3/2011 | Carson | |
| 2011/0071530 A1 | 3/2011 | Carson | |
| 2011/0071532 A1 | 3/2011 | Carson | |
| 2011/0071533 A1 | 3/2011 | Metzger et al. | |
| 2011/0092804 A1 | 4/2011 | Schoenefeld et al. | |
| 2011/0093086 A1 | 4/2011 | Witt et al. | |

FOREIGN PATENT DOCUMENTS

| | | |
|---|---|---|
| CA | 2501041 | 4/2004 |
| CA | 2505371 | 5/2004 |
| CA | 2505419 | 6/2004 |
| CA | 2506849 | 6/2004 |
| CA | 2546958 | 6/2005 |
| CA | 2546965 | 6/2005 |
| CA | 2588907 | 6/2006 |
| CA | 2590534 | 6/2006 |
| CH | 117960 | 5/1927 |
| CN | 1630495 A | 6/2005 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| DE | 337437 | 5/1921 |
| DE | 2830566 A1 | 1/1980 |
| DE | 3339259 C1 | 3/1985 |
| DE | 3447365 A1 | 7/1986 |
| DE | 3717871 A1 | 12/1988 |
| DE | 3925488 A1 | 2/1990 |
| DE | 3902249 A1 | 8/1990 |
| DE | 4016704 C1 | 9/1991 |
| DE | 04219939 A1 | 12/1993 |
| DE | 4421153 A1 | 12/1995 |
| EP | 0114505 A1 | 8/1984 |
| EP | 97001 A1 | 9/1986 |
| EP | 0326768 A2 | 8/1989 |
| EP | 337901 A1 | 10/1989 |
| EP | 0579868 A2 | 1/1994 |
| EP | 645984 A1 | 4/1995 |
| EP | 0650706 A1 | 5/1995 |
| EP | 756735 A1 | 8/1998 |
| EP | 0916324 A2 | 5/1999 |
| EP | 908836 A3 | 12/1999 |
| EP | 1020734 | 7/2000 |
| EP | 1013231 A3 | 8/2000 |
| EP | 904158 A1 | 7/2002 |
| EP | 1 321 097 A2 | 6/2003 |
| EP | 1321107 A1 | 6/2003 |
| EP | 709061 A1 | 7/2003 |
| EP | 1136041 A3 | 10/2003 |
| EP | 1437102 A1 | 7/2004 |
| EP | 1444957 A1 | 8/2004 |
| EP | 1486900 A1 | 12/2004 |
| EP | 1498851 A1 | 1/2005 |
| EP | 1669033 A1 | 6/2006 |
| EP | 1348393 B1 | 3/2007 |
| FR | 1111677 | 3/1956 |
| FR | 2429582 A1 | 1/1980 |
| FR | 2659226 A1 | 9/1991 |
| FR | 2721195 A1 | 12/1995 |
| FR | 2768916 A1 | 4/1999 |
| FR | 2819168 A1 | 7/2002 |
| GB | 2094590 A | 9/1982 |
| GB | 2197790 A | 6/1988 |
| GB | 2426200 A | 11/2006 |
| GB | 2437003 A | 10/2007 |
| GB | 2442441 A | 4/2008 |
| JP | 59157715 A | 9/1984 |
| JP | 60231208 A | 11/1985 |
| JP | 2002291706 | 10/2002 |
| KR | 20050072500 A | 7/2005 |
| KR | 20050084024 A | 8/2005 |
| RU | 2083179 C1 | 7/1997 |
| RU | 2113182 C1 | 6/1998 |

| | | |
|---|---|---|
| RU | 2125835 C1 | 2/1999 |
| RU | 2138223 C1 | 9/1999 |
| RU | 2175534 C2 | 11/2001 |
| RU | 2187975 C1 | 8/2002 |
| TW | 1231755 | 5/2005 |
| WO | 8807840 A1 | 10/1988 |
| WO | 8909028 A1 | 10/1989 |
| WO | 8911257 | 11/1989 |
| WO | 9107139 A1 | 5/1991 |
| WO | 9325157 | 12/1993 |
| WO | 9325157 A1 | 12/1993 |
| WO | 9413218 A1 | 6/1994 |
| WO | 9528688 | 10/1995 |
| WO | 9528688 A1 | 10/1995 |
| WO | 9607361 | 3/1996 |
| WO | 9729703 | 8/1997 |
| WO | 9732671 A1 | 9/1997 |
| WO | 9800072 A1 | 1/1998 |
| WO | 9832384 | 7/1998 |
| WO | 9901073 A1 | 1/1999 |
| WO | 9932045 | 7/1999 |
| WO | 9952473 A1 | 10/1999 |
| WO | 9959106 A1 | 11/1999 |
| WO | 0170142 A1 | 9/2001 |
| WO | 0184479 A1 | 11/2001 |
| WO | 0218019 | 3/2002 |
| WO | 0226145 A2 | 4/2002 |
| WO | 2002/37935 | 5/2002 |
| WO | 0236024 A1 | 5/2002 |
| WO | 02/067783 A2 | 9/2002 |
| WO | 02096268 A2 | 12/2002 |
| WO | 03/042968 A1 | 5/2003 |
| WO | 0351210 A2 | 6/2003 |
| WO | 0351211 A1 | 6/2003 |
| WO | 03/077101 A2 | 9/2003 |
| WO | 04000139 A1 | 12/2003 |
| WO | 2004032806 A9 | 5/2004 |
| WO | 2004017842 A3 | 6/2004 |
| WO | 2004049981 A1 | 6/2004 |
| WO | 2004051301 A2 | 6/2004 |
| WO | 2004/061744 | 7/2004 |
| WO | 2004/069041 A2 | 8/2004 |
| WO | 2004/070580 | 8/2004 |
| WO | 2004075771 A1 | 9/2004 |
| WO | 2004078069 A2 | 9/2004 |
| WO | 2004084725 A1 | 10/2004 |
| WO | 2005027755 A1 | 3/2005 |
| WO | 2005051240 A1 | 6/2005 |
| WO | 2005053564 A3 | 6/2005 |
| WO | 2005077039 A2 | 8/2005 |
| WO | 2005/084558 | 9/2005 |
| WO | 2005051239 A1 | 9/2005 |
| WO | 2005084558 | 9/2005 |
| WO | 2005084558 A1 | 9/2005 |
| WO | 2005099636 A1 | 10/2005 |
| WO | 2005/119505 | 12/2005 |
| WO | 2006058057 A2 | 6/2006 |
| WO | 2006060795 | 6/2006 |
| WO | 2006060795 A1 | 6/2006 |
| WO | 2006092600 A1 | 9/2006 |
| WO | 2006127486 A2 | 11/2006 |
| WO | 2006134345 A1 | 12/2006 |
| WO | 2007041375 A2 | 4/2007 |
| WO | 2007053572 A2 | 5/2007 |
| WO | 2007062079 A2 | 5/2007 |
| WO | 2007/097854 | 8/2007 |
| WO | 2007092841 A2 | 8/2007 |
| WO | 2007097854 | 8/2007 |
| WO | 2007097853 A3 | 12/2007 |
| WO | 2007137327 A1 | 12/2007 |
| WO | 2007145937 A2 | 12/2007 |
| WO | 2007097854 A3 | 1/2008 |
| WO | 2008014618 A1 | 2/2008 |
| WO | 2008021494 A2 | 2/2008 |
| WO | 2008040961 A1 | 4/2008 |
| WO | 2008044055 A1 | 4/2008 |
| WO | 2008101090 A2 | 8/2008 |
| WO | 2008112996 A1 | 9/2008 |
| WO | 2008117028 A1 | 10/2008 |
| WO | 2008140748 A1 | 11/2008 |
| WO | 2009001083 A1 | 12/2008 |
| WO | 2009025783 A1 | 2/2009 |
| WO | 2009045960 A1 | 4/2009 |
| WO | 2009111512 A3 | 10/2009 |
| WO | 2009129063 A1 | 10/2009 |
| WO | 2009129067 A1 | 10/2009 |
| WO | 2010033431 A1 | 3/2010 |

OTHER PUBLICATIONS

Accuracy of CT-Based Patient Specific Total Knee Arthroplasty Instruments; AAHKS 20th Annual Meeting, Submission Record, Submission ID # 4177, Apr. 14, 2010.

"Personalised image-based templates for intra-operative guidance," Proceedings of the Institution of Mechanical Engineers, Part H: Journal of Engineering in Medicine, 111-118.

"Computer-assisted Total Kneed Arthroplasty Using Patient-specific Templating," Clinical Orthopaedics and Related Research, 444, 184-192, (12 pages).

"OrthoTAIX for Orthopaedic Surgery," Available at http://www.surgitaix.com/Products/OrthoTAIX/OrthoTAIX.pdf, 2 pages.

"Computer-Integrated Orthopaedic Surgery: Connection of Planning and Execution in Surgical Intervention," Computer Integrated Surgery, 451-463.

"Computer Assisted Orthopaedic Surgery with Image Based Individual Templates," Clinical Orthopaedics and Related Research 354, 28-38 (15 pages).

"CT Image-Based Planning and Execution of Interventions in Orthopedic Surgery Using Individual Templates—Experimental Results and Aspects of Clinical Applications," Computer Assisted Orthopaedic Surgery, L. P. Nolte and R. Ganz, eds, 42-52, Hogrefe & Huber Publishing.

"A home-based pedometer-driven walking program to increase physical actifvity in order adults with osteoarthritis of the knee: a preliminary study," Journal of the American Geriatrics Society, vol. 51, No. 3, 6 pages.

"Measuring functional abilities of patients with knee problems; rationale and construction of the DynaPort knee test," Knee Surgery, Sports Traumatology, Arthroscopy, vol. 10, pages 204-212.

"Automated physical activity monitoring: validation and comparison with physiological and self-report measures," Psychophysiology, vol. 30, pages 296-305.

"Xbus Master: Portable multi-sensor system." [Online] <http://www.xsens.com/index.php?mainmenu=products&submenu=human_motion&subsubmenu=Xbus_Master>, 2 pages.

"MTx: 3DOF Orientation Tracker." [Online] <http://www.xsens.com/index.php?mainmenu=products&submenu=human_motion&subsubmenu=MTx>, 2 pages.

"Moven - inertial motion capturing." [Online] <http://www.xsens.com/index.php?mainmenu=products&submenu=human_motion&subsubmenu=Moven>, 4 pages.

"Insall/Burstein II Surgical Technique," Constrained Condylar Modular Knee System, (18 pages).

European Search Report for European Patent Application No. 10150487.6-2310, May 12, 2010, 6 pages.

European Search Report for European Patent Application No. 09171188.7-2310, Sep. 24, 2010, 7 pages.

International Preliminary Report on Patentability for International Patent Publication No. PCT/US2008/078143, Apr. 15, 2010, 8 pages.

Chinese First Office Action, Chinese Patent Application No. 200880118434.4, Sep. 7, 2011, 12 pages.

* cited by examiner

CUSTOMIZED PATIENT SURGICAL PLAN

BACKGROUND

Surgeons are turning to minimally invasive orthopaedic procedures. Because such procedures generally restrict the surgeon's ability to see the operative area, surgeons generally rely on computer systems, such as computer assisted orthopaedic surgery (CAOS) systems, to assist in the surgical operations. CAOS systems assist surgeons in the performance of orthopaedic surgical procedures by, for example, displaying images illustrating surgical steps of the surgical procedure being performed. Typical CAOS systems are stand-alone systems that are neither integrated with, nor configured to communicate with, other electronic systems of networks such as, for example, hospital networks. As such, typical CAOS systems are unable to access electronic data, such as medical records and the like, stored in the other electronic systems and networks. Moreover, typical CAOS systems require a surgeon to enter considerable amount of data and other responses in order to configure, calibrate and/or drive the system during the surgical procedure.

SUMMARY

The present invention may comprise a system, apparatus and/or method that may have one or more of the following features and/or steps, which alone or in any combination may comprise patentable subject matter.

A method of a vendor to create a surgical plan for a patient of a healthcare facility that is external to the vendor is disclosed. The method may include receiving, from the healthcare facility external to the vendor, a surgical plan request that includes data relevant to the patient and a surgical procedure to be performed upon the patient. The method may also include creating, in response to receiving the surgical plan request, a surgical plan that has been customized for the patient per data of the surgical plan request. Creating the surgical plan may include generating instructions for the surgical plan that configure a computer assisted orthopaedic surgery system to assist in the surgical procedure upon the patient. The surgical plan may also be generated based upon one or more medical images that depict at least one bone of the patient.

The method may further include sending the surgical plan to the healthcare facility for execution. Sending the surgical plan may include transmitting the surgical plan to the healthcare facility via a network. Sending the surgical plan may also include mailing the surgical plan to the healthcare facility.

In one embodiment, the method may further include receiving from the healthcare facility a modified surgical plan request that requests modifications to the surgical plan. The method in such an embodiment may further include modifying the surgical plan to obtain a modified surgical plan in response to receiving the modified surgical plan request, and sending the surgical plan to the healthcare facility for execution.

Some embodiments of the method may include creating the surgical plan in accordance with surgical procedures associated with a particular surgeon in response to the surgical plan request requesting that the surgical plan be constructed in accordance with surgical procedures associated with the particular surgeon. Similarly, other embodiments of the method may include creating the surgical plan in accordance with surgical procedures associated with a particular institution in response to the surgical plan request requesting that the surgical plan be constructed in accordance with surgical procedures associated with the particular institution.

A machine readable medium comprising a plurality of instructions is also provided. The instructions, in response to being executed, may result in a computing device creating a surgical plan for an orthopaedic surgical procedure based upon a surgical plan request that includes an image of a bone of a patient. The instructions may further result in the computing device transmitting the surgical plan to a healthcare facility via a network. The instructions of the machine readable medium may also result in the computing device generating the surgical plan such that the surgical plan upon being loaded by a computer assisted orthopaedic surgery system configures the computer assisted orthopaedic surgery system to assist in the orthopaedic surgical procedure.

In another embodiment, the instructions may result in the computing device generating the surgical plan such that the surgical plan includes instructions that in response to being executed by a computer assisted orthopaedic surgery system results in the computer assisted orthopaedic surgery system assisting in the orthopaedic surgical procedure. Execution of the instructions may further result in the computing device generating the surgical plan such that in response to being executed by a computer assisted orthopaedic surgery system results in the computer assisted orthopaedic surgery system displaying images of individual surgical steps which form the orthopaedic surgical procedure.

In yet another embodiment, the instructions of the machine readable medium result in the computing device modifying the surgical plan to obtain a modified surgical plan in response to a request to modify the surgical plan. Further, the instructions of this embodiment may result in the computing device transmitting the modified surgical plan to the healthcare facility via the network.

The instructions may further result in the computing device creating the surgical plan in accordance with a particular surgeon in response to a request for the surgical plan be constructed in accordance with the particular surgeon. The instructions may also result in the computing device creating the surgical plan in accordance with a particular institution in response to a request for the surgical plan be constructed in accordance with surgical procedures associated with the particular institution.

A system for generating surgical plans is also provided. The system may include a client, a surgical plan system and a computer assisted orthopaedic surgery system. The client may generate a surgical plan request that includes data relevant to a patient and an orthopaedic surgical procedure to be performed upon the patient. The surgical plan system may receive the surgical plan request and may generate a surgical plan that has been customized based upon the data of the surgical plan request. The computer assisted orthopaedic surgery system may assist a surgeon performing the orthopaedic surgical procedure per the surgical plan generated by the surgical plan system.

In one embodiment, the surgical plan system may be located at a vendor and the computer assisted orthopaedic surgery system may be located at a healthcare facility. Further, the surgical plan system may select an orthopaedic implant for the orthopaedic surgical procedure based upon at least one image of the surgical plan request. The computer assisted orthopaedic surgery system may also display images of individual surgical steps which form the orthopaedic surgical procedure in response to executing the surgical plan generated by the surgical plan system.

BRIEF DESCRIPTION OF THE DRAWINGS

The invention described herein is illustrated by way of example and not by way of limitation in the accompanying figures. For simplicity and clarity of illustration, elements illustrated in the figures are not necessarily drawn to scale. For example, the dimensions of some elements may be exaggerated relative to other elements for clarity. Further, where considered appropriate, reference labels have been repeated among the figures to indicate corresponding or analogous elements.

DETAILED DESCRIPTION OF THE DRAWINGS

Figure 1:
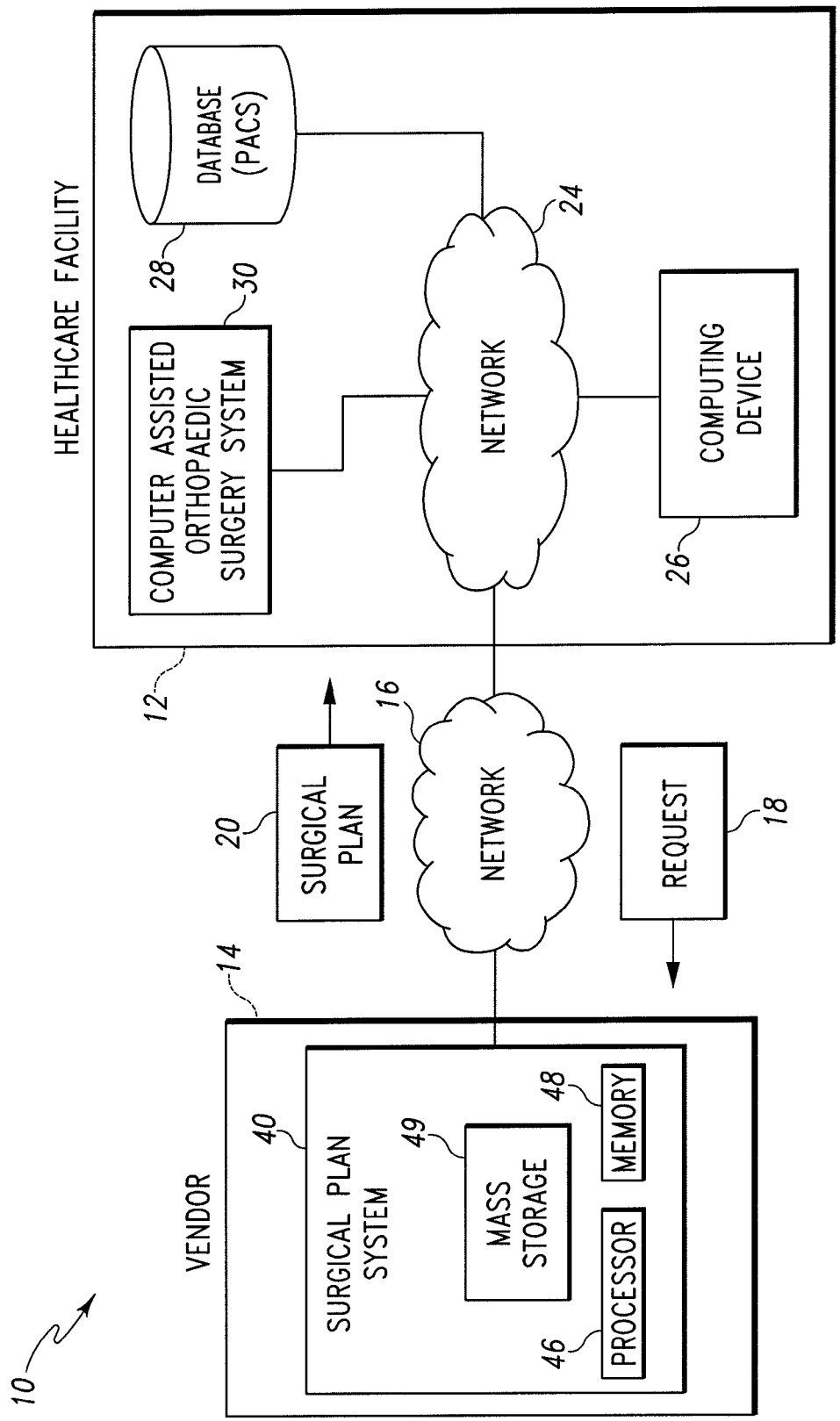
FIG. 1 shows a system for generating surgical plans that have been customized for a particular patient.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

In the following description, numerous specific details such as logic implementations, opcodes, means to specify operands, resource partitioning/sharing/duplication implementations, types and interrelationships of system components, and logic partitioning/integration choices are set forth in order to provide a more thorough understanding of the present disclosure. It will be appreciated, however, by one skilled in the art that embodiments of the disclosure may be practiced without such specific details. In other instances, control structures, gate level circuits and full software instruction sequences have not been shown in detail in order not to obscure the invention. Those of ordinary skill in the art, with the included descriptions, will be able to implement appropriate functionality without undue experimentation.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM), random access memory (RAM), magnetic disk storage media, optical storage media, flash memory devices, and others.

Referring to FIG. 1, a system 10 that customizes and executes surgical plans is shown. The system 10 may include a vendor 14 that provides the custom surgical plans 20. The system 10 may further include a healthcare facility 12 and a network 16 that communicatively couples the vendor 14 and the healthcare facility 12. As discussed in more detail below, the healthcare facility 12 may include a computer assisted orthopedic surgery (CAOS) system 30 that executes and/or assists caregiver(s) in the execution of custom surgical plans 20 provided by the vendor 14.

The network 16 may include one or more wide area networks (WAN), local area networks (LAN), and/or publicly-accessible global networks such as, for example, the Internet. In addition, the network 16 may include one or more wired networks and/or wireless networks. As such, the network 16 may include routers, switches, computers, communication links, and other networking components that cooperate to operatively couple the vendor 14 and the healthcare facility 12.

The healthcare facility 12 may include a network 24, computing devices or clients 26, databases 28, and CAOS systems 30. Similar to the network 16, the healthcare facility network 24 may include wide area networks (WAN), local area networks (LAN), publicly-accessible global networks such as, for example, the Internet, and/or other types of networks. In addition, the healthcare facility network 24 may include wired networks and/or wireless networks. As such, the healthcare facility network 24 may include routers, switches, computers, communication links, and other networking components that cooperate to operatively couple computing devices 26, medical databases 28, CAOS systems 30, and possibly other network enabled devices of the healthcare facility 12.

The computing devices 26 may display data and receive input from caregivers of the healthcare facility 12 such as, for example, doctors, nurses, anesthesiologists, and surgeons. The computing devices 26 may include a variety of different computing devices such as, for example, servers, desktop computers, laptop computers, handheld computers, personal data assistants, mobile phones, and possibly other computing devices. A computing device 26 is illustrated in FIG. 1 as being physically located within the healthcare facility 12; however, in some embodiments, one or more of the computing devices 26 may remotely access the healthcare facility network 24 from locations external to the healthcare facility 12. Such embodiments may enable caregivers to order and/or otherwise define custom surgical plans 20 while the caregiver is away from the healthcare facility 12.

The databases 28 may store personal data, medical data, and/or other data associated with patients of the healthcare facility 12. In one embodiment, the databases 28 may include a Patient Archiving Communications System (PACS) that stores medical images for patients of the healthcare facility 12.

The vendor 14 may include a surgical plan system 40. The surgical plan system 40 may receive a request 18 for a surgical plan via network 16 from the healthcare facility 12, generate a surgical plan 20 that has been customized based upon information of the received request, and provide the healthcare facility 12 with the custom surgical plan 20 via network 16.

The surgical plan system 40 may include one or more computing devices and associated software, middleware, and/or firmware that cooperate to perform the surgical plan customizations described herein. In particular, the surgical plan system 40 may include one or more processors 46, one or more memory devices 48, and one or more mass storage devices 49.

The processor 46 may include a microprocessor, microcontroller, discrete processing circuitry (e.g., a collection of logic devices), general purpose integrated circuit(s), and/or application specific integrated circuit(s) (i.e., ASICs). The memory device 48 may include volatile memory devices such as, for example, dynamic random access memory (DRAM) and static random access memory (SRAM). The memory device 48 may further include non-volatile memory devices such as, for example, various types of read-only memory (i.e., ROM) and FLASH memory devices. The memory devices 48 generally store data and/or instructions that the processors 46 are currently processing and/or expected to process in the near future.

The mass storage devices 49 may include hard drives, DVD drives, CD drives, database servers and/or other devices suitable for storing large amounts of data and/or instructions. The mass storage devices 49 in one embodiment store data and instructions in a non-volatile manner; however, other embodiments may include mass storage devices such as large disk caches that store data in a volatile manner. The mass storage devices 49 generally store data and/or instructions that the processor 46 is not expected to process in the near future and/or is desirable to retain for extended periods of time. In addition to the above mentioned components, the surgical plan system 40 may include other devices and circuitry typically found in computing devices such as, for example, displays, input/output devices, and/or other peripheral components.

Figure 2:
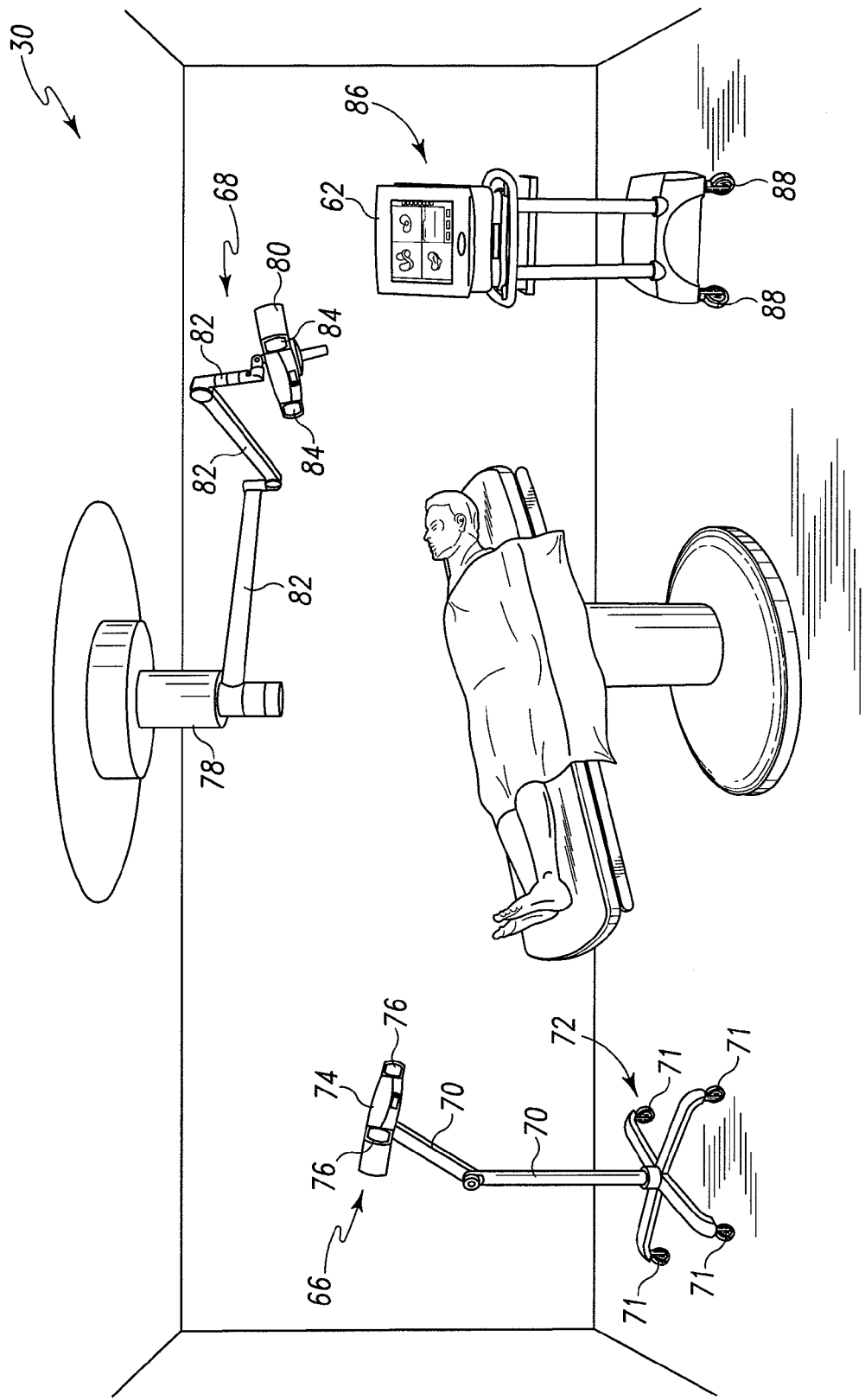
FIG. 2 shows a computer assisted orthopaedic surgery (CAOS) system of FIG. 1.

One embodiment of a CAOS system 30 is shown in FIG. 2. As shown, the CAOS system 30 may include a computing device 62 and a camera unit such as, for example, mobile camera unit 66 and a fixed camera unit 68. In some embodiments, the CAOS system 30 may include both types of camera units 66, 68. The mobile camera unit 66 includes a stand 70 coupled with a base 72. The base 72 may include a number of wheels 71 to allow the mobile camera unit 66 to be repositioned within a hospital room. The mobile camera unit 66 may include a camera head 74. The camera head 74 may include two cameras 76. The camera head 74 may be positionable relative to the stand 70 such that the field of view of the cameras 76 may be adjusted.

The fixed camera unit 68 is similar to the mobile camera unit 66 and includes a base 78, a camera head 80, and an arm 82 coupling the camera head 80 with the base 78. In some embodiments, other peripherals, such as display screens, lights, and the like, may also be coupled with the base 78. The camera head 80 includes two cameras 84. The fixed camera unit 68 may be coupled to a ceiling, as shown in FIG. 2, or a wall of the hospital room. Similar to the camera head 74 of the camera unit 66, the camera head 80 may be positionable relative to the arm 82 such that the field of view of the cameras 84 may be adjusted. The camera units 66, 68 are communicatively coupled with the computing device 62. The computing device 62 may be mounted on or otherwise coupled with a cart 86 having a number of wheels 88 to allow the computing device 62 to be positioned near the surgeon during the performance of the orthopaedic surgical procedure.

Figure 3:
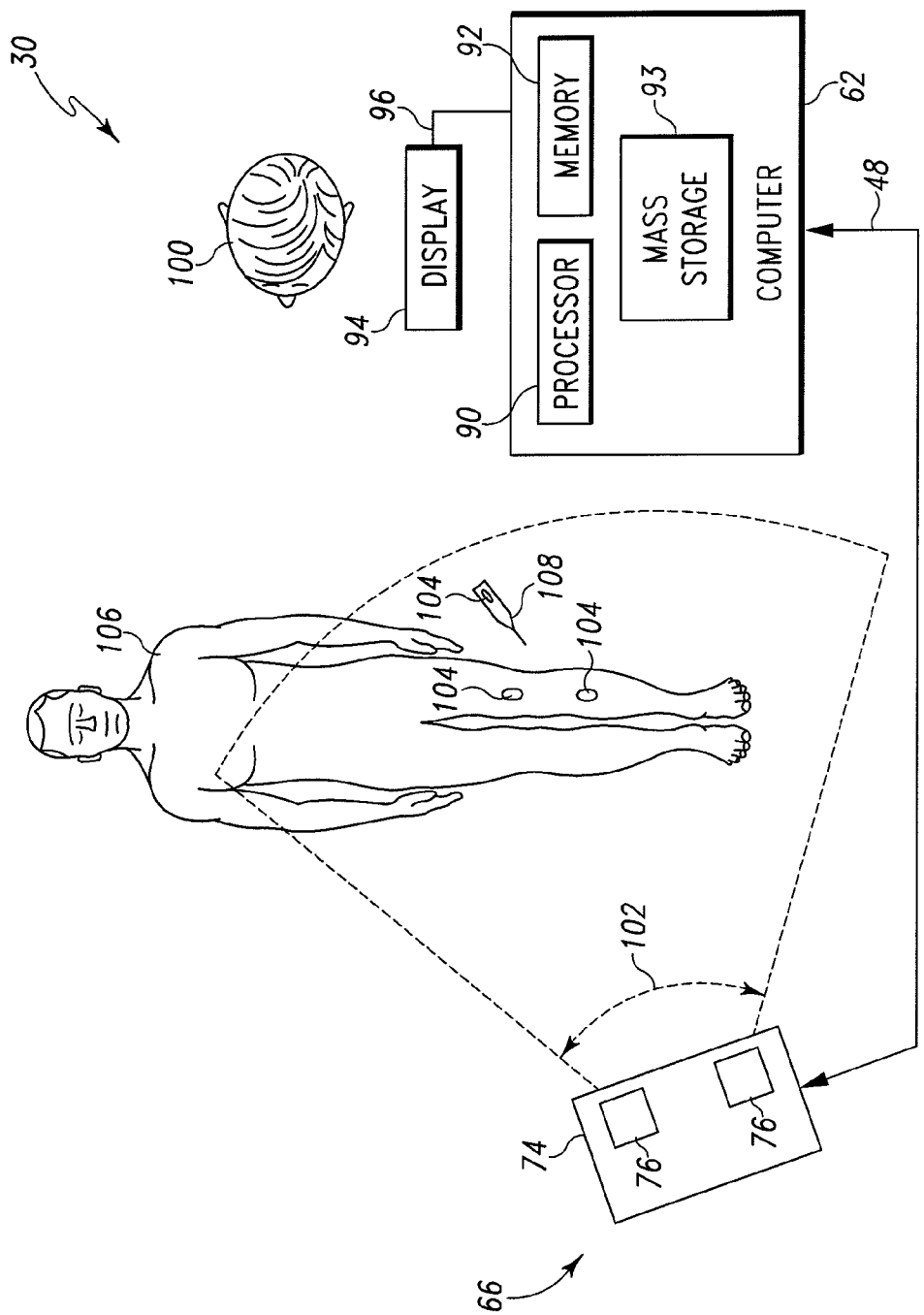
FIG. 3 shows more details regarding the CAOS system of FIG. 2.

Referring now to FIG. 3, additional details of one embodiment of a CAOS system 30 are shown. In particular, the computing device 62 may include a processor 90, a memory device 92, and mass storage device 93. The processor 90 may include a microprocessor, a microcontroller, discrete processing circuitry (e.g., a collection of logic devices), general purpose integrated circuit(s), and/or application specific integrated circuit(s) (i.e., ASICs). The memory device 92 may include volatile memory devices such as, for example, dynamic random access memory (DRAM) and static random access memory (SRAM). The memory device 92 may further include non-volatile memory devices such as, for example, various types of read-only memory (i.e., ROM) and FLASH memory devices. The memory devices 92 generally store data and/or instructions that the processors 90 are currently processing and/or expected to process in the near future.

The mass storage devices 93 may include hard drives, DVD drives, CD drives, database servers and/or other devices suitable for storing large amounts of data and/or instructions. The mass storage devices 93 in one embodiment may store data and instructions in a non-volatile manner; however, other embodiments may include mass storage devices such as large disk caches that store data in a volatile manner. The mass storage devices generally store data and/or instructions that the processor 90 is not expected to process in the near future and/or is desirable to retain for extended periods of time.

The computing device 62 is communicatively coupled with a display device 94. Although illustrated in FIG. 3 as separate from the computing device 62, the display device 94 may form a portion of the computer computing device 62 in some embodiments. Additionally, in some embodiments, the display device 94 or an additional display device may be positioned away from the computing device 62. For example, the display device 94 may be positioned upon the ceiling or wall of the operating room wherein the orthopaedic surgical procedure is to be performed. Additionally or alternatively, the display device 94 may include a virtual display such as a holographic display, a body mounted display such as a heads-up display, and/or other types of displays. The computing device 62 may also include input devices such as a keyboard and/or a mouse for providing data input to the computing device 62. The display device 94 may include a touch-screen display device capable of receiving inputs from an orthopaedic surgeon 100. That is, the surgeon 100 may provide input data to the computing device 62, such as making a selection from a number of on-screen choices, by simply touching the screen of the display device 94.

The computing device 62 may be communicatively coupled to the camera unit 66 (and/or 68). Although only the mobile camera unit 66 is shown in FIG. 3, the fixed camera unit 68 may alternatively be used or may be used in addition to the mobile camera unit 66.

Figure 4:
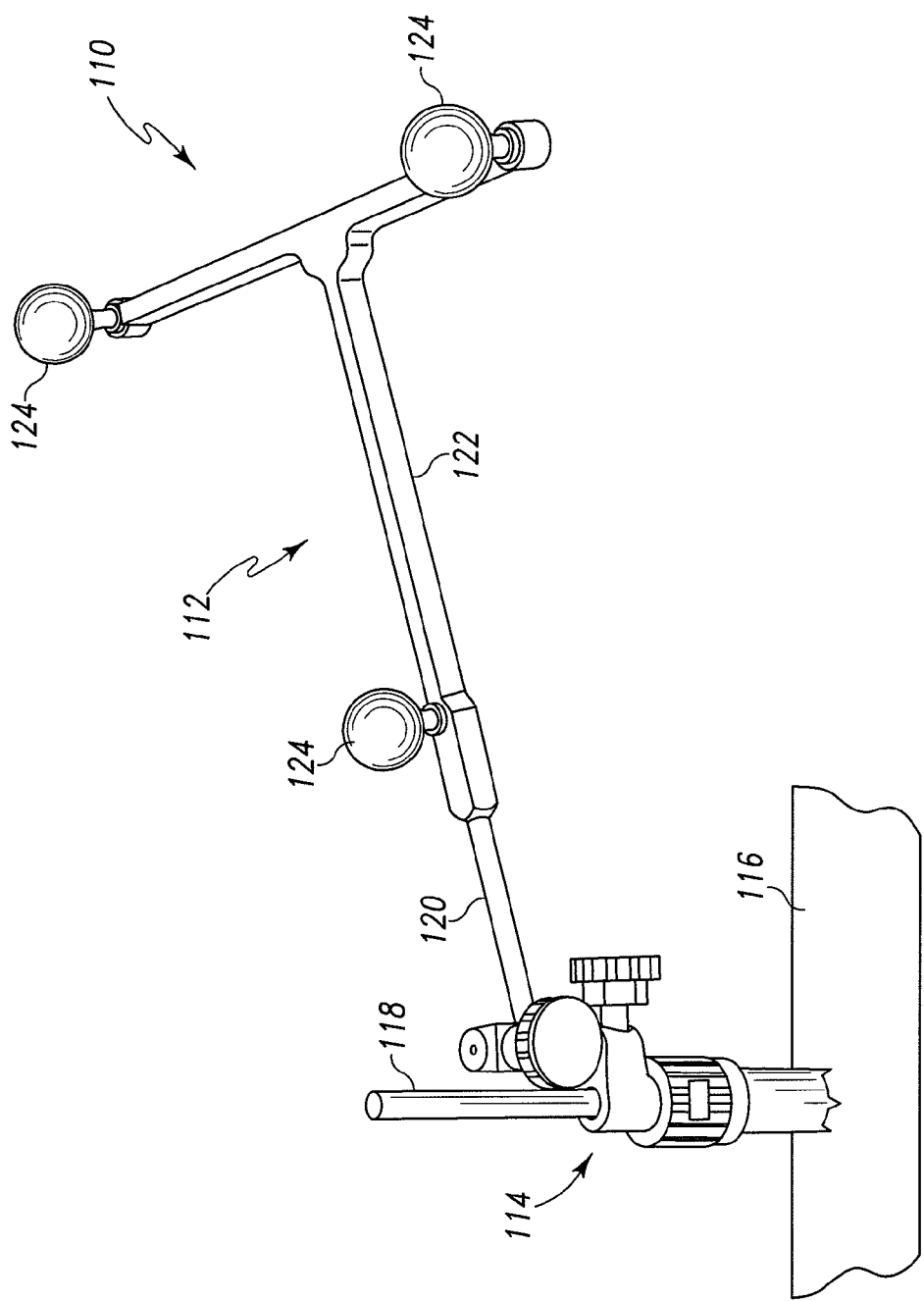
FIG. 4 shows a bone locator tool for use with the CAOS system of FIG. 2.

The CAOS system 30 may also include sensors or reference arrays 104 which may be coupled to relevant bones of a patient 106 and/or with orthopaedic surgical tools 108. For example, as illustrated in FIG. 4, a tibial array 110 includes a reference array 112 and bone clamp 114. The bone clamp 114 may be coupled with a tibia bone 116 of the patient 106 using a Schantz pin 118, but other types of bone clamps may be used. The reference array 112 may be coupled with the bone clamp 114 via an extension arm 120. The reference array 112 may include a frame 122 and three reflective elements 124. The reflective elements 124 in one embodiment are spherical, but may have other geometric shapes. Additionally, in other embodiments sensor arrays having more than three reflective elements may be used. The reflective elements 112 may be positioned in a predefined configuration that enables the computing device 62 to determine the identity of the tibial array 110 based on the configuration. That is, when the tibial array 110 is positioned in a field of view 102 of the camera head 74, as shown in FIG. 3, the computing device 62 may determine the identity of the tibial array 110 based on the images received from the camera head 74. Additionally, based on the relative position of the reflective elements 114, the computing device 62 may determine the location and orientation of the tibial array 110 and, accordingly, the tibia 116 to which the array 110 is coupled.

Figure 5:
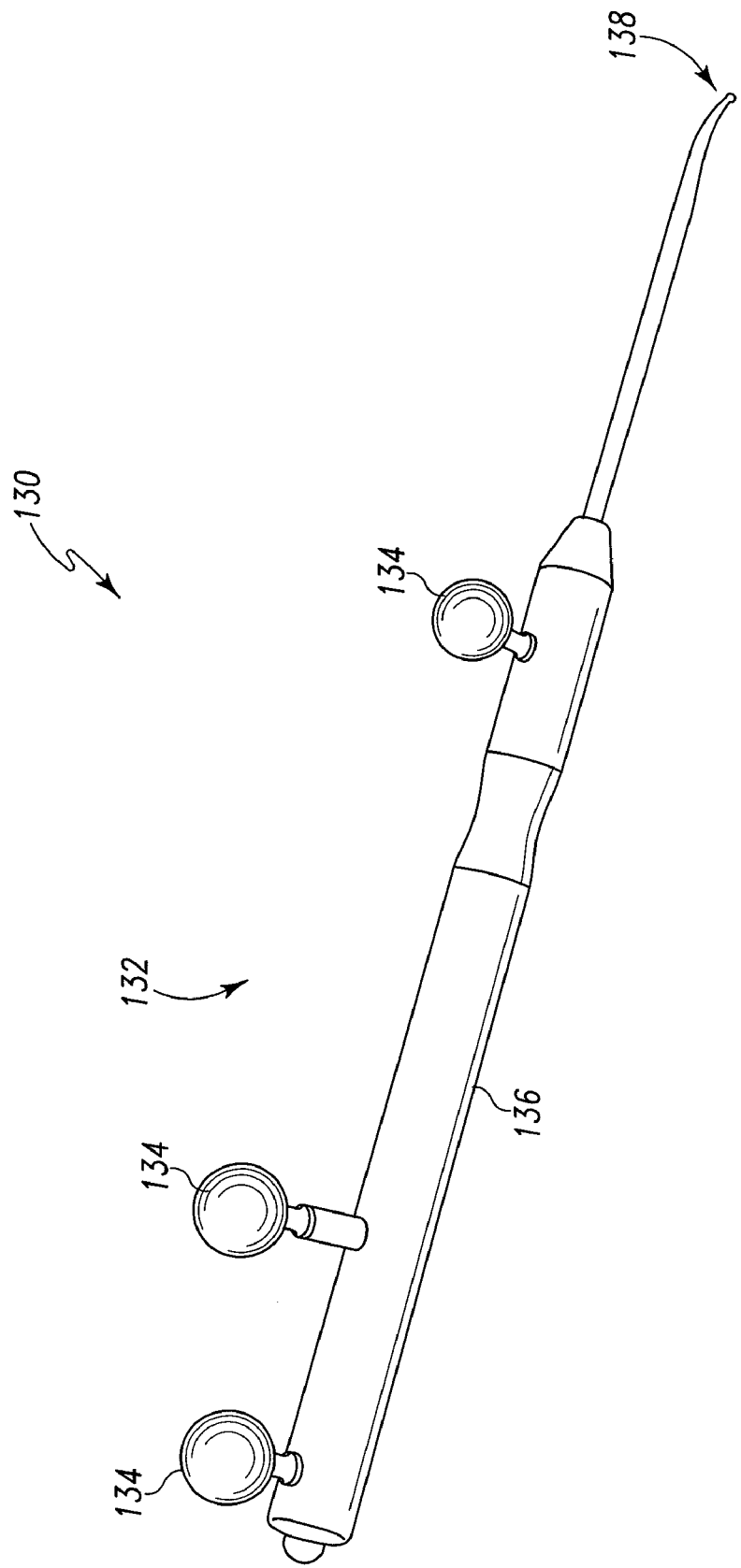
FIG. 5 shows a registration tool for use with the CAOS system of FIG. 2.
Figure 6:
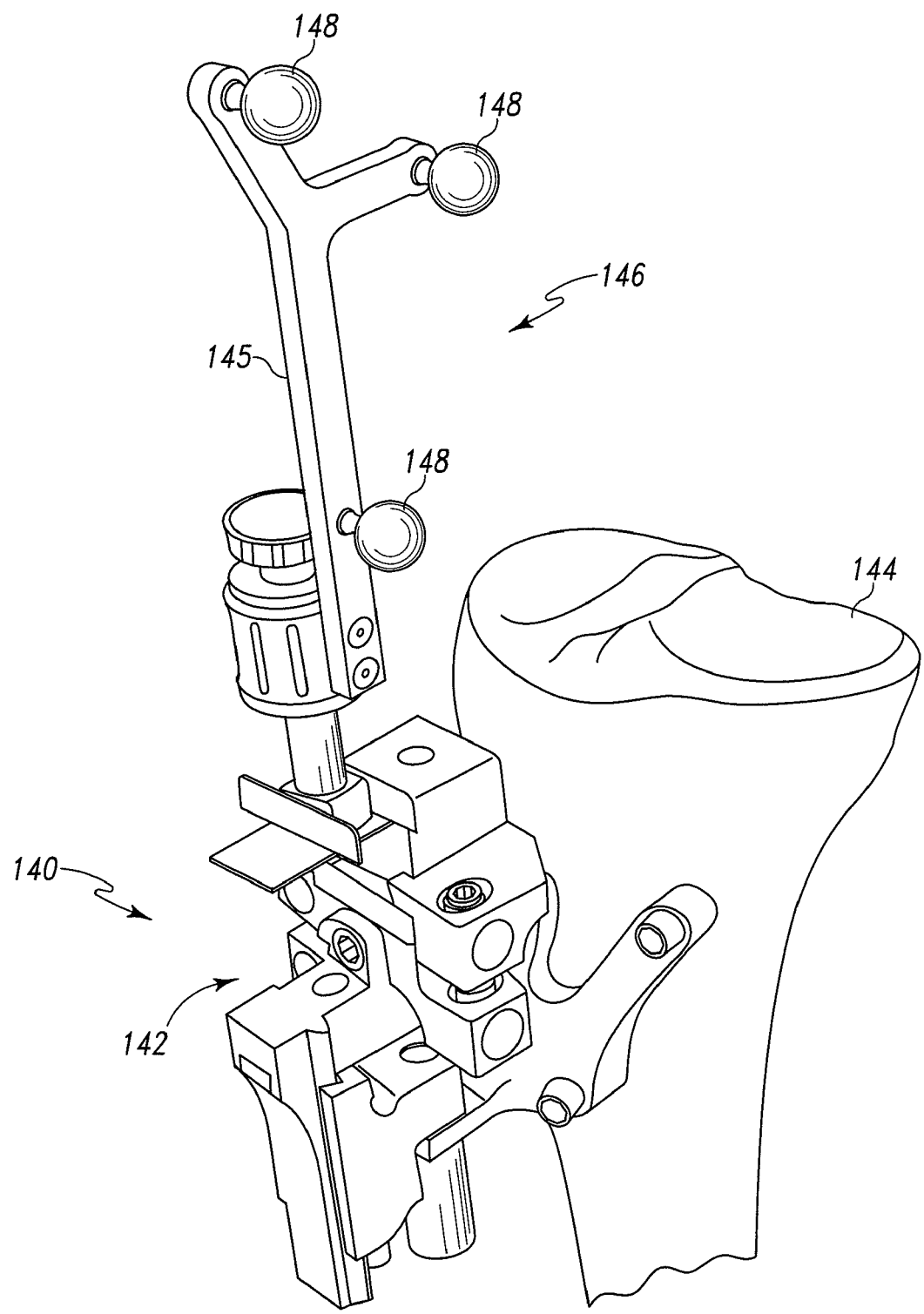
FIG. 6 shows an orthopaedic surgical tool for use with the system of FIG. 2.

Reference arrays may also be coupled to other surgical tools. For example, a registration tool 130, as shown in FIG. 5, may be used to register points of a bone. The registration tool 130 may include a sensor array 132 having three reflective elements 134 coupled with a handle 136 of the tool 130. The registration tool 130 may also include a pointer end 138 that is used to register points of a bone. The reflective elements 134 may be positioned in a configuration that enables the computing device 62 to determine the identity of the registration tool 130 and its relative location (i.e., the location of the pointer end 138). Additionally, reference arrays may be used on other surgical tools such as a tibial resection jig 140, as illustrated in FIG. 6. The jig 140 may include a resection guide portion 142 that is coupled with a tibia bone 144 at a location of the bone 144 that is to be resected. The jig 140 may include a reference array 146 that is coupled with the portion 142 via a frame 145. The reference array 146 may include three reflective elements 148 that may be positioned in a configuration that enables the computing device 62 to determine the identity of the jig 140 and its relative location (e.g., with respect to the tibia bone 144).

The CAOS system 30 may assist the orthopaedic surgeon 100 in an orthopaedic surgical procedure including, for example, a total knee replacement procedure. To do so, the computing device 62 and/or the display device 94 may be positioned within the view of the surgeon 100. As discussed above, the computing device 62 may be coupled with a movable cart 86 to facilitate such positioning. The camera unit 66 (and/or camera unit 68) may be positioned such that the field of view 102 of the camera head 74 covers the portion of a patient 106 upon which the orthopaedic surgical procedure is to be performed, as shown in FIG. 3.

During the performance of the orthopaedic surgical procedure, a custom surgical plan 20 may include one or more instructions that program or otherwise configure the computing device 62 of the CAOS system 30 to display images of the individual surgical procedure steps which form the orthopaedic surgical procedure being performed. The images may be graphically rendered images or graphically enhanced photographic images. For example, the images may include three dimensional rendered images of the relevant anatomical portions of a patient. The surgeon 100 may interact with the computing device 62 to display the images of the various surgical steps in sequential order. In addition, the surgeon may interact with the computing device 62 to view previously displayed images of surgical steps, selectively view images, instruct the computing device 62 to render the anatomical result of a proposed surgical step or procedure, or perform other surgical related functions. For example, the surgeon 100 may view rendered images of the resulting bone structure of different bone resection procedures. In this way, the custom surgical plan 20 may configure the CAOS system 30 to provide a surgical "walk-through" customized to the patient 106 that the surgeon 100 may follow while performing the surgical procedure.

In one embodiment, the custom surgical plan 20 may include an ordered selection of instructional images that depict individual surgical steps that make up at least a portion of the orthopaedic surgical procedure to be performed. The instructional images may include images of surgical tools and associated text information, graphically rendered images of surgical tools and relevant patient anatomy, and/or other images and/or text information that assist the surgeon during the surgical procedure. The instructional images may be stored in an electronic library, which may be embodied as, for example, a database, a file folder or storage location containing separate instructional images and an associated look-up table, hard-coded information stored in the memory device 92, mass storage device 93, and/or other electronic storage devices accessible via the network 24 of the healthcare facility 12. Accordingly, a surgical plan 20 may include among other things an ordered selection of instructional images that are displayed to the surgeon 100 via the display device 94 such that the instructional images provide a surgical "walk-through" of the procedure or portion thereof. The surgical plan 20 may also include a number of surgical sub-step images, some of which may or may not be displayed to and performed by the surgeon 100 based on selections chosen by the surgeon 100 during the performance of the orthopaedic surgical procedure.

In some embodiments, the surgeon 100 may also interact with the computing device 62 to control various devices of the CAOS system 30. For example, the surgeon 100 may interact with the CAOS system 30 to control user preferences or settings of the display device 94. Further, the computing device 62 may prompt the surgeon 100 for responses. For example, the computing device 62 may prompt the surgeon to inquire if the surgeon has completed the current surgical step, if the surgeon would like to view other images, and/or other surgical procedure inquiries.

As discussed above, the computing devices 26, the database 28, and/or the CAOS system 30 may communicate with each other and/or with the communication network 16 via the local network 24. For example, the surgeon's computer 26 may be used to access data, such as medical images, stored on the database 28. Additionally or alternatively, the CAOS system 30 may be used to generate pre-operative orthopaedic surgical plans, surgical notes created during an orthopaedic surgery, medical images of a patient's bone (and soft tissue) and/or orthopaedic implants coupled thereto, and/or other data. Such data generated via the CAOS system 30 may be stored in the database 28 by, for example, transmitting the data from the CAOS system 30 to the database 28 via the network 24. Additionally, other medical devices typically found in a hospital or other healthcare facility may be used to generate medical images of a bone (and, in some embodiments, soft tissue) of the patient. Such medical images may also be stored in the database 28. The medical images may be embodied as any type of medical image providing a visual indication of a relevant bone or bones (and soft tissue if desired) of a patient. For example, the medical images may be embodied as any number of X-ray images, magnetic resonance imaging (MRI) images, computerized tomography (CT) images, or the like. Regardless, such medical images may be stored in the database 28 along with associated data relevant to the particular medical images. Such associated data may include, but is not limited to, the patient's name and other patient identification information, date of the images, surgeon's or doctor's name, the name of the hospital or healthcare facility wherein the medical images were generated, and the like.

Figure 7:
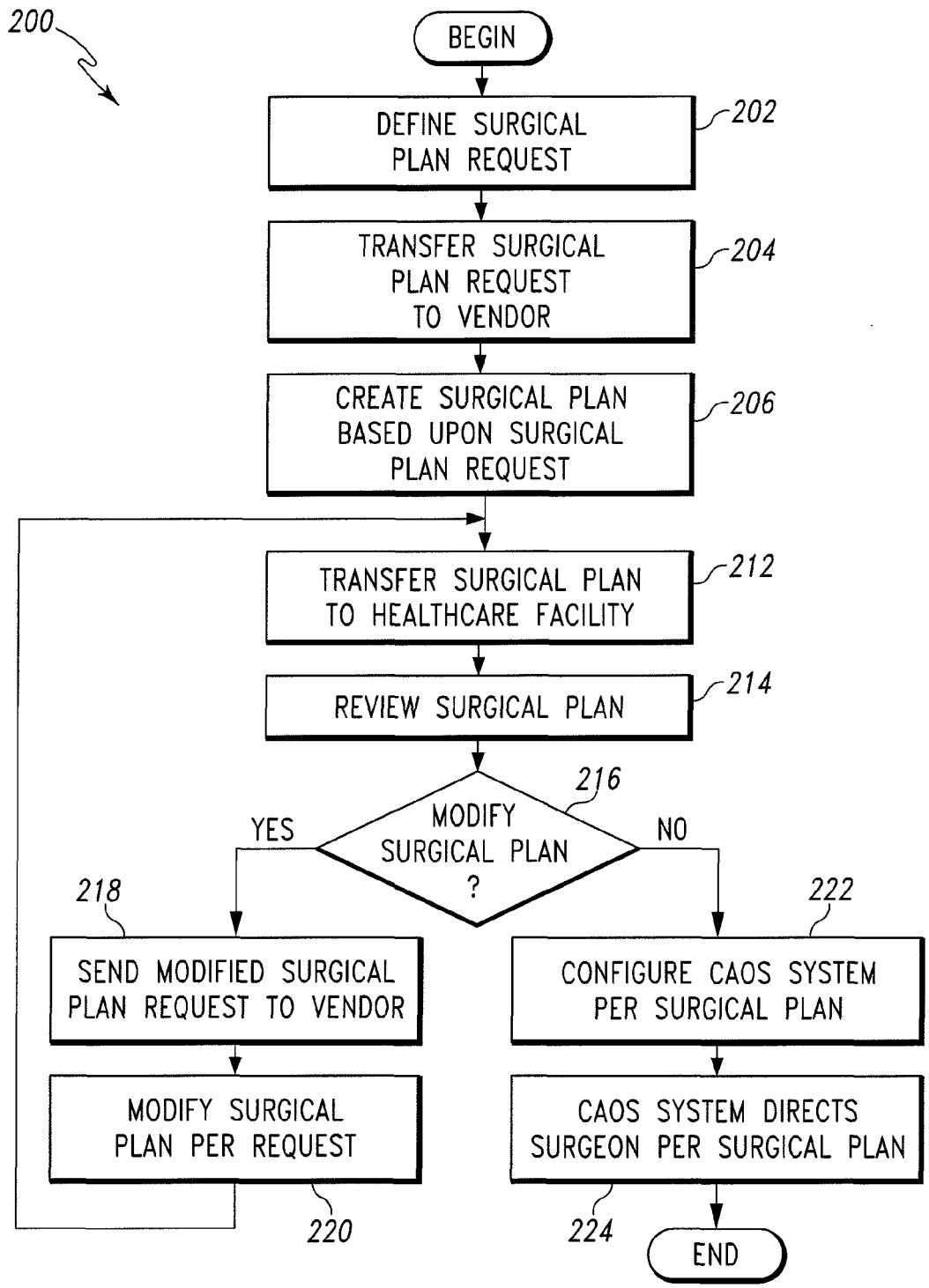
FIG. 7 shows a method for generating, modifying and executing a custom surgical plan.

In operation, the vendor 14 of the custom surgical plan system 10 may receive a request for surgical plans for a patient, may generate a surgical plan that has been customized for the patient, and may provide the custom surgical plan for the patient to the healthcare facility 12. A method 200 of performing a surgical procedure in accordance with a custom surgical plan 20 is shown in FIG. 7. The method 200 may begin in block 202 with defining a surgical plan request 18 for a custom surgical plan 20 that has been customized for a particular patient. To this end, one or more caregivers of the healthcare facility 12 may define the surgical plan request 18 by using one or more computing devices or clients 26. In particular, the caregivers may enter or otherwise collect surgical plan request data that is relevant to the surgical procedure to be performed and the particular patient receiving the surgical procedure. The surgical plan request data may include any data relevant to the surgical plan being requested, any data related to the orthopaedic surgical procedure to be performed, any data related to the patient on which the orthopaedic surgical procedure to be performed, and/or any other data useful for customizing the orthopaedic surgical procedure to the patient. For example, the request data may include, but is not limited to, the type of orthopaedic surgical procedure to be performed, the type of orthopaedic implant to be used, rendered images of the relevant anatomical portions of the patient, digital templates of the orthopaedic implants and/or planned resection lines, pre-operative notes, diagrams, historic patient data, X-rays, medical images, patient medical records, patient identification data, and/or any other data useful for customizing the orthopaedic surgical procedure to the patient.

Typically, medical images are generated pre-operatively in preparation for an orthopaedic surgical procedure. The medical images may include any number of medical images. For example, the medical images may include a medical image of the relevant bone(s) taken along the sagittal plane of the patient's body and a medical image of the relevant bone(s) taken along the coronal plane of the patient's body. The medical images may include X-ray images, magnetic resonance imaging (MRI) images, computerized tomography (CT) images, and/or any other type of image capable of providing indicia of the relevant bone or bones. Such imaging devices may be located in the healthcare facility 12 or may be located remote therefrom. The imaging devices may or may not be communicatively coupled to the healthcare facility 12.

At block 202, a surgeon may use a computing device 26 that may be located in the healthcare facility 12 or external to the healthcare facility 12 to define the surgical plan request 18. In particular, the surgeon may define the surgical plan request 18 by entering and/or collecting the request data via the computing device 26. In some embodiments, the surgeon may operate the computing device 26 to retrieve, from various information servers of the hospital facility 12 such as databases 28, data relevant to the surgical plan 20 such as, for example, patient medical history, X-rays, medical images and/or other related data as described above. In addition, the surgeon may enter constraint data that may limit, restrict, or otherwise affect the generation of the surgical plan 20 for the patient. For example, the constraint data may include the surgeon's preference for an orthopaedic implant type, the surgeon's preference for particular parts of the implant, the degree of acceptable orthopedic implant sizes (e.g., a restriction on the range of implant sizes that may be recommended), the amount of bone that will be resected, the planned location and/or orientation of the orthopaedic implant, fixation type (e.g., cement or cementless), material type, finish, and other features such as head size and other preferences such as metal-on-metal, metal-on-ceramic, ceramic-on-ceramic, metal-on-poly, or the like.

The constraint data may further identify a branded surgical procedure that has been branded or otherwise associated with a particular surgeon, healthcare facility, university and/or another person or institution. For example, a surgeon may request a surgical plan 20 for a knee replacement in the style of Dr. Brown. Similarly, a surgeon may request an Oxford Clinic arthroplasty of the knee. In this manner, a surgeon may obtain the latest surgical plans 20 that will enable the surgeon to use techniques perfected by other surgeons or developed by other institutions, thus increasing the rate at which such new procedures may be propagated through the medical community.

At block 204, the surgical plan request 18 may be transferred from the healthcare facility 12 to the vendor 14. In one embodiment, a computing device 26 or CAOS system 30 of the healthcare facility 12 may transmit the surgical plan request 18 to the surgical plan system 40 of the vendor 14 via network 16. However, other manners of providing the surgical plan request 18 to the surgical plan system 40 are also contemplated. For example, instead of a computing device 26 or CAOS system 30 transmitting the surgical plan request 18 to the surgical plan system 40, the surgical plan system 40 may retrieve the request from a computing device 26, CAOS system 30, and/or another device via network 16. Further, the surgical plan system 40 may also support receiving surgical plan requests 18 from storage devices such as CD-ROMs, DVD-ROMs, thumb drives, floppy disks, portable hard drives. In such an embodiment, a caregiver of the healthcare facility 12 may store the surgical plan request 18 to the storage device and mail or otherwise deliver the storage device to the vendor 14. The vendor 14 may then upload the request from the storage device to the surgical plan system 40.

The surgical plan system 40 at block 206 may create a surgical plan 20 based upon the constraints and other data provided by the surgical plan request 18. In creating the surgical plan 20, the surgical plan system 40 may perform a digital templating procedure on medical images of the surgical plan request 18 to determine an orthopaedic implant to recommend to the surgeon or healthcare facility for use with relevant bone(s) of the patient. To do so, the surgical plan system 40 may be configured to determine relevant aspects of the patient's bone or bony anatomy from the medical images. For example, the surgical plan system 40 may determine one or more mechanical axis of the relevant bones, determine one or more resection planes of the relevant bones, locate particular features of the relevant bones, and/or the like. Based on such determinations, the surgical plan system 40 may select an appropriate orthopaedic implant type and size that also satisfies the implant constraint data of the surgical plan request 18. The surgical plan system 40 may also be configured to determine recommended range of sizes of the orthopaedic implant. For example, in some embodiments, the surgical plan system 40 may be configured to determine an orthopaedic implant within a range of plus or minus two sizes. For example, the surgical plan system 40 may recommend an orthopaedic implant of a size 5+/−2 sizes (i.e., a range of size 3 to size 7).

In creating the surgical plan 20, the surgical plan system 40 may also retrieve a digital template(s) of the orthopaedic implant. The digital template may be retrieved from, for example, the memory device 48, mass storage device 49 or from any other storage location capable of storing a number of digital templates. The digital template may include one or more two-dimensional and/or three-dimensional electronic renderings of the orthopaedic implant selected for the surgical procedure, or components thereof, that is capable of being superimposed on a medical image of the patient. For example, a digital template may be embodied as a two-dimensional or three-dimensional electronic rendering of an orthopaedic knee implant component that is capable of being superimposed or otherwise incorporated into a medical image of a tibia or femur bone of the patient. As discussed in more detail below, the digital template may be used in conjunction with indicia of the determined aspects or features of the relevant bones such as lines or other indicia of the mechanical axis or resection points/planes of the relevant bones.

Figure 8:
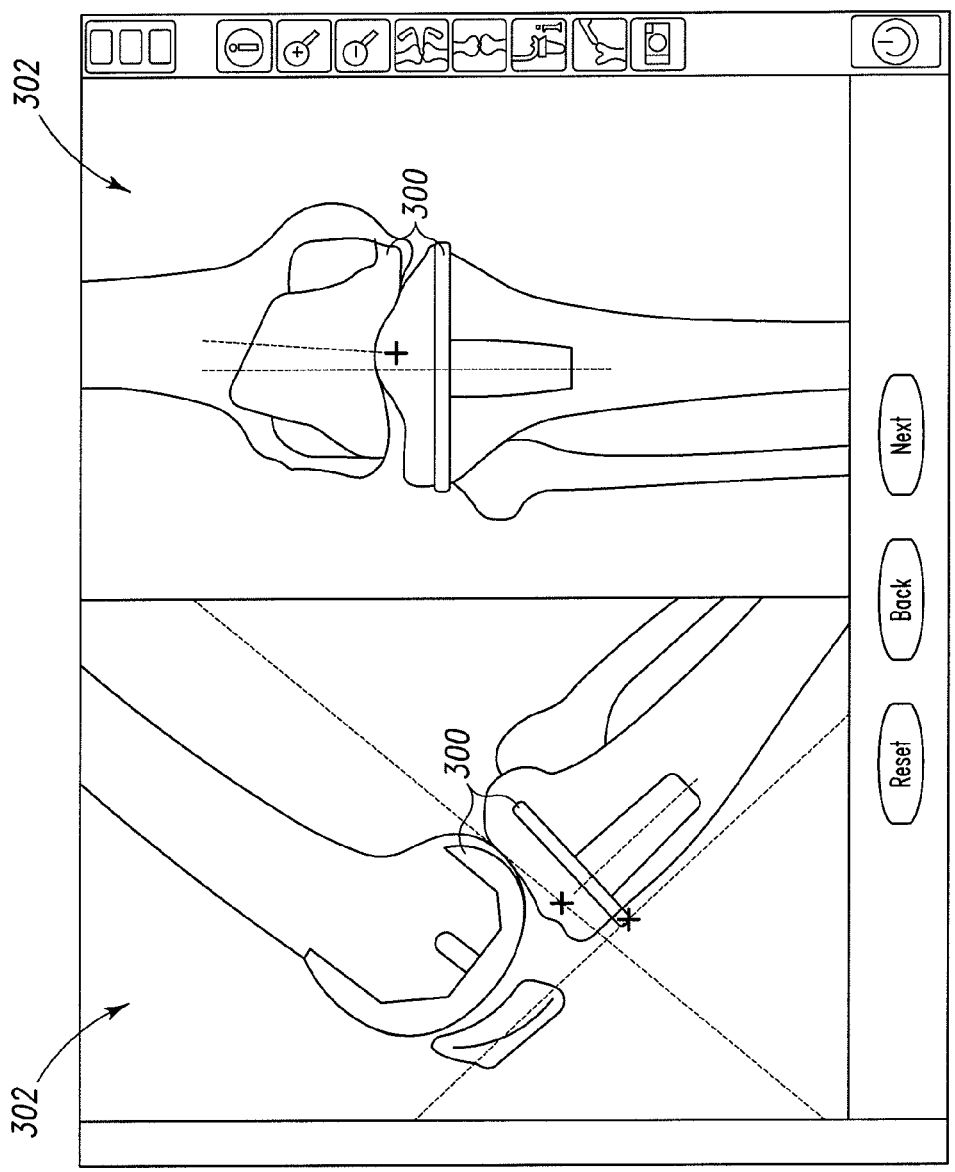
FIG. 8 shows a medical image having a digital template of an orthopaedic implant superimposed thereon.

The surgical plan system 40 may superimpose or otherwise incorporate the digital template into the medical images of the surgical plan request 20. For example, in one illustrative embodiment, as illustrated in FIG. 8, a digital template 300 of an orthopaedic implant is superimposed on a medical image 302 of a bone of the patient. As discussed above, although the illustrative digital template 300 is illustrated as a two-dimensional template, in other embodiments, the digital template may include any number of two-dimensional and/or three-dimensional electronic renderings of the orthopaedic implant.

The surgical plan system 40 may be configured to use any suitable algorithm and data of the surgical plan request 18 to determine a recommended location and orientation of the orthopaedic implant, as represented by the digital template, with respect to the patient's bone. For example, if implant constraint data provides an estimated amount of resection of the patients' bone, the surgical plan system 40 may be configured to position the digital template in the medical images based on such estimated resection. In addition, any one or more of the aspects of the bone as determined above may be used to determine the proper positioning of the digital template. For example, the determined mechanical axis, resection planes, and/or other determined aspects of the relevant bones may be used to determined the proper positioning of the digital template. In this way, the surgical plan system generates a number of digital templated medical images having indicia of the relevant bone's of the patient and indicia of the recommended orthopaedic implant positioned in a location and orientation.

Although described above as an automated process, in some embodiments, the creation of the surgical plan 20 may be a semi-automated or a manual process. For example, a technician such as a CAD operator or medical technician of the vendor 14 may determine the aspects of the relevant bones such as the mechanical axis, the resection lines, and/or other particular features of the relevant bones. The technician may edit the medical images such that indicia of such aspects are superimposed or otherwise incorporated into the medical images. For example, the technician may electronically draw the mechanical axes and/or resection lines. Once such aspects of the relevant bones are determined, the surgical plan system 40 may be configured to determine a recommended orthopaedic implant and create a custom surgical plan 20 based on the aspects of the relevant bones determined by the technician, retrieve a digital template of the recommended orthopaedic implant, and superimpose or otherwise incorporate the digital template into the medical image based on, for example, the determined aspects of the relevant bones.

In other embodiments, the custom surgical plan 40 may be manually created by the vendor 14. In such embodiments, a technician may determine the aspects of the relevant bones, incorporate indicia of such aspects into the medical images (e.g., draw the mechanical axis, resection lines, etc. of the relevant bones), and determine a recommended orthopaedic implant and surgical plan 20 based on such aspects. The technician may then manually superimpose or otherwise incorporate a digital template of the recommended orthopaedic implant into the medical images. The technician may locate and orientate the digital template based on the determined aspects of the relevant bones. For example, the technician may position the digital template of the recommended orthopaedic implant in the medical image using a suitable CAD software program or the like.

Regardless, the surgical plan system 40 at block 212 may transfer the surgical plan 20 to the healthcare facility 16. In one embodiment, surgical plan system 40 may transmit the custom surgical plan 20 to the healthcare facility 12 via the network 16. The custom surgical plan 20 may be stored in a database 28 of the healthcare facility 12 that is accessible to the CAOS systems 30. However, the custom surgical plan 20 may alternatively or additionally be stored in computing devices 26 or CAOS systems 30 of the healthcare facility 12.

At block 214, the surgeon may review the surgical plan via a computer device 26 and/or CAOS system 30. For example, the surgeon may review the digital templated medical images to determine if the digital template of the orthopaedic implant is properly located with respect to the patient's bone, if the type of recommended orthopaedic implant is correct, if a larger or smaller orthopaedic implant size is more desirable, and/or the like. Furthermore, the surgeon may review the series of operations defined by the surgical plan 20.

At block 216, the surgeon may decide based upon his review of the surgical plan 20 to have the vendor 14 modify the surgical plan 20. If the surgeon decides to have the vendor 14 change the surgical plan 20, the surgeon at block 218 may modify aspects of the surgical plan request 18 such as, for example, providing further constraints or directives regarding the custom surgical plan 20 and transfer the modified surgical plan request 18 to the vendor 14. For example, the surgeon may modify a digital templated medical images and/or other data of the received surgical plan 20 and transmit the modified digital templated medical images and/or other data to the surgical plan system 40.

The surgical plan system 40 at block 220 may modify the surgical plan 20 per the modified surgical plan request 18. The surgical plan system 40 may perform any number of corrective procedures on the surgical plan 20 based upon the modified digital templated medical images and/or recommendation data (e.g., the range of recommended orthopaedic implant sizes) received from the surgeon in process step 218.

The surgical plan system 40 may then return to block 212 in order to transmit the modified surgical plan 20 to the healthcare facility 12. In this manner, the vendor 14 and the surgeon may modify the surgical plan 20 for the patient until the surgeon is satisfied with the surgical plan 20.

If the surgeon is satisfied with the custom surgical plan 20 for the patient, the CAOS system 30 may be configured based upon the custom surgical plan 20 at block 222. The custom surgical plan 20 may configure the CAOS system 30 using various different techniques. The computing device 62 of the CAOS system 30 may receive the surgical plan 20 directly from the vendor 14. The computing device 62 of the CAOS system 30 may load the surgical plan 20 from a computing device 26 and/or database 28 of the healthcare facility 12. The computing device 62 of the CAOS system 30 may load the surgical plan 20 from a machine readable medium such as CD-ROM, DVD-ROM, thumb drive, floppy or other portable storage device created by the vendor 14 or a computing device 26 of the healthcare facility. In another embodiment, a surgical plan 20 may comprise a document of instructions for a caregiver such as a technician to manually input into the computing device 62 of the CAOS system 30 prior to the orthopaedic surgical procedure.

At block 224, the CAOS system 30 directs a surgeon through the orthopaedic surgical procedure per the custom surgical pan 20 for the patient. In particular, the computing device 62 of the CAOS system 30 per the surgical plan 20 may control the display device 94 to display images of the individual surgical steps which form the orthopaedic surgical procedure.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

What is claimed is:

1. A method of a vendor to create a surgical plan for a patient of a healthcare facility that is external to the vendor, comprising
  receiving, with a surgical plan system, a surgical plan request transmitted from the healthcare facility, the surgical plan request including (i) data relevant to the patient, (ii) data relevant to a surgical procedure to be performed upon the patient, and (iii) preference data that identifies surgical preferences related to the surgical procedure of an orthopaedic surgeon,
  generating, with the surgical plan system and based on the surgical plan request, an order of surgical procedure instructional images that define surgical steps of the surgical procedure,
  creating, in response to receiving the surgical plan request, a surgical plan on the surgical plan system, the surgical plan having been customized for the patient per data of the surgical plan request, the surgical plan including a plurality of instructions that configure a computer assisted orthopedic surgery system to assist in the surgical procedure upon the patient by displaying the surgical procedure instructional images in the generated order, and
  sending, from the surgical plan system, the surgical plan to the healthcare facility for execution on the computer assisted orthopaedic surgery system.

2. The method of claim 1, wherein sending comprises transmitting the surgical plan to the healthcare facility via a network.

3. The method of claim 1, wherein sending comprises mailing the surgical plan to the healthcare facility.

4. The method of claim 1, further comprising generating, on the surgical plan system, the plurality of instructions based upon one or more medical images that depict at least one bone of the patient.

5. The method of claim 1, further comprising
  receiving, on the surgical plan system, from the healthcare facility a modified surgical plan request that requests modifications to the surgical plan,
  modifying, on the surgical plan system, the surgical plan to obtain a modified surgical plan in response to receiving the modified surgical plan request, and
  sending, from the surgical plan system, the surgical plan to the healthcare facility for execution.

6. The method of claim 1, further comprising creating, on the surgical plan system, the surgical plan in accordance with surgical procedures associated with a particular surgeon in response to the surgical plan request requesting that the surgical plan be constructed in accordance with surgical procedures associated with the particular surgeon.

7. The method of claim 1, further comprising creating, on the surgical plan system, the surgical plan in accordance with surgical procedures associated with a particular institution in response to the surgical plan request requesting that the surgical plan be constructed in accordance with surgical procedures associated with the particular institution.

8. A tangible, machine readable medium comprising a plurality of instructions, that in response to being executed, result in a computing device
  receiving a surgical plan request that comprises (i) data relevant to a patient including an image of a bone of the patient, (ii) data relevant to an orthopaedic surgical procedure to be performed upon the patient, and (iii) preference data that identifies surgical preferences related to the surgical procedure of an orthopaedic surgeon,
  generating, based on the surgical plan request, an order of surgical procedure instructional images that define surgical steps of the surgical procedure,
  creating a surgical plan for the orthopaedic surgical procedure based upon the surgical plan request, the surgical plan including plurality of instructions that configure a computer assisted orthopedic surgery system to assist in the surgical procedure upon the patient by displaying the surgical procedure instructional images in the generated order, and
  transmitting the surgical plan to a healthcare facility via a network for execution on the computer assisted orthopaedic surgery system.

9. The tangible, machine readable medium of claim 8, wherein the plurality of instructions further result in the computing device
  modifying the surgical plan to obtain a modified surgical plan in response to a request to modify the surgical plan, and
  transmitting the modified surgical plan to the healthcare facility via the network.

10. The tangible, machine readable medium of claim 8, wherein the plurality of instructions further result in the computing device creating the surgical plan in accordance with a particular surgeon in response to a request for the surgical plan to be constructed in accordance with the particular surgeon.

11. The tangible, machine readable medium of claim 8, wherein the plurality of instructions further result in the computing device creating the surgical plan in accordance with a particular institution in response to a request for the surgical plan to be constructed in accordance with surgical procedures associated with the particular institution.

12. A system for generating surgical plans, comprising
  a computer assisted orthopaedic surgery system to assist a surgeon performing an orthopaedic surgical procedure per a surgical plan,
  a client computing device to generate a surgical plan request that includes (i) data relevant to a patient including an image of a bone of the patient, (ii) data relevant to the orthopaedic surgical procedure to be performed upon the patient, and (iii) preference data that identifies surgical preferences related to the surgical procedure of an orthopaedic surgeon, and
  a surgical plan system to receive the surgical plan request and to generate (i) an order of surgical procedure instructional images that define surgical steps of the surgical procedure based on the surgical plan request and (ii) the surgical plan that has been customized based upon the data of the surgical plan request, the surgical plan including plurality of instructions that configure the computer assisted orthopedic surgery system to assist in the surgical procedure upon the patient by displaying the surgical procedure instructional images in the generated order.

13. The system of claim 12, wherein the surgical plan system is located at a vendor and the computer assisted orthopaedic surgery system is located at a healthcare facility.

* * * * *

UNITED STATES PATENT AND TRADEMARK OFFICE
CERTIFICATE OF CORRECTION

| | | |
|---|---|---|
| PATENT NO. | : 8,265,949 B2 | Page 1 of 1 |
| APPLICATION NO. | : 11/862746 | |
| DATED | : September 11, 2012 | |
| INVENTOR(S) | : Haddad | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 996 days.

Signed and Sealed this
Twenty-ninth Day of December, 2015

Michelle K. Lee
*Director of the United States Patent and Trademark Office*